US008057758B2

(12) United States Patent
Bedingham et al.

(10) Patent No.: US 8,057,758 B2

(45) **Date of Patent: *Nov. 15, 2011**

(54) VARIABLE VALVE APPARATUS AND METHODS

(75) Inventors: William Bedingham, Woodbury, MN (US); Barry W. Robole, Woodville, WI (US); Ranjani V. Parthasarathy, Woodbury, MN (US); Katya Ericson, Fairburn, GA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/719,704

(22) Filed: Mar. 8, 2010

(65) Prior Publication Data

US 2010/0167304 A1 Jul. 1, 2010

Related U.S. Application Data

(63) Continuation of application No. 11/684,656, filed on Mar. 12, 2007, now abandoned, which is a continuation of application No. 10/852,642, filed on May 24, 2004, now abandoned, which is a continuation-in-part of application No. 10/734,717, filed on Dec. 12, 2003, now Pat. No. 7,322,254.

(60) Provisional application No. 60/532,523, filed on Dec. 24, 2003.

(51) Int. Cl.
*C12Q 1/68* (2006.01)

(52) U.S. Cl. ........ 422/506; 422/504; 422/537; 422/538; 435/6.1; 435/287.6; 435/288.4; 435/288.5

(58) Field of Classification Search ........................ None
See application file for complete search history.

(56) References Cited

U.S. PATENT DOCUMENTS

| | | | |
|---|---|---|---|
| 3,157,635 | A | 11/1964 | Tanaka et al. |
| 4,153,661 | A | 5/1979 | Ree et al. |
| 4,373,519 | A | 2/1983 | Errede et al. |
| 4,399,009 | A | 8/1983 | Chisholm |

(Continued)

FOREIGN PATENT DOCUMENTS

| | | |
|---|---|---|
| DE | 197 31 670 | 6/2000 |

(Continued)

OTHER PUBLICATIONS

Wang, Hailin et al., *Short Protocols in Molecular Biology*, Science Press, (1998), 2 pgs.

(Continued)

*Primary Examiner* — In Suk Bullock
*Assistant Examiner* — Timothy G Kingan
(74) *Attorney, Agent, or Firm* — Nicole J. Einerson

(57) ABSTRACT

Sample processing devices with variable valve structures and methods of using the same are disclosed. The valve structures allow for removal of selected portions of the sample material located within the process chamber. Removal of the selected portions is achieved by forming an opening in a valve septum at a desired location. The valve septums may be large enough to allow for adjustment of the location of the opening based on the characteristics of the sample material in the process chamber. If the sample processing device is rotated after the opening is formed, the selected portion of the material located closer to the axis of rotation exits the process chamber through the opening. The remainder of the sample material cannot exit through the opening because it is located farther from the axis of rotation than the opening.

20 Claims, 4 Drawing Sheets

U.S. PATENT DOCUMENTS

| | | | |
|---|---|---|---|
| 4,399,235 | A | 8/1983 | Raley, Jr. et al. |
| 4,460,642 | A | 7/1984 | Errede et al. |
| 4,483,920 | A | 11/1984 | Gillespie et al. |
| 4,539,256 | A | 9/1985 | Shipman et al. |
| 4,565,663 | A | 1/1986 | Errede et al. |
| 4,619,897 | A | 10/1986 | Hato et al. |
| 4,726,989 | A | 2/1988 | Mrozinski |
| 4,737,560 | A | 4/1988 | Heilmann et al. |
| 4,757,014 | A | 7/1988 | Hendrickson et al. |
| 4,780,367 | A | 10/1988 | Lau et al. |
| 4,810,381 | A | 3/1989 | Hagen et al. |
| 4,839,296 | A | 6/1989 | Kennedy et al. |
| 4,855,234 | A | 8/1989 | Hendrickson et al. |
| 4,906,378 | A | 3/1990 | Hagen et al. |
| 4,923,978 | A | 5/1990 | McCormick |
| 4,954,444 | A | 9/1990 | Eveleigh et al. |
| 4,957,943 | A | 9/1990 | McAllister et al. |
| 4,971,736 | A | 11/1990 | Hagen et al. |
| 5,010,183 | A | 4/1991 | Macfarlane |
| 5,011,861 | A | 4/1991 | Coull et al. |
| 5,015,373 | A | 5/1991 | Carr et al. |
| 5,019,232 | A | 5/1991 | Wilson et al. |
| 5,030,697 | A | 7/1991 | Hugl et al. |
| 5,071,610 | A | 12/1991 | Hagen et al. |
| 5,079,155 | A | 1/1992 | Cox et al. |
| 5,108,597 | A | 4/1992 | Funkenbusch et al. |
| 5,141,634 | A | 8/1992 | Carr et al. |
| 5,147,539 | A | 9/1992 | Hagen et al. |
| 5,182,016 | A | 1/1993 | Funkenbusch et al. |
| 5,182,083 | A | 1/1993 | Barker et al. |
| 5,182,377 | A | 1/1993 | Manos et al. |
| 5,183,705 | A | 2/1993 | Birkholz et al. |
| 5,187,066 | A | 2/1993 | Becker et al. |
| 5,187,083 | A | 2/1993 | Mullis |
| 5,200,471 | A | 4/1993 | Coleman et al. |
| 5,205,929 | A | 4/1993 | Carr et al. |
| 5,207,915 | A | 5/1993 | Hagen et al. |
| 5,234,809 | A | 8/1993 | Boom et al. |
| 5,238,621 | A | 8/1993 | Hagen et al. |
| 5,264,184 | A | 11/1993 | Aysta et al. |
| 5,271,833 | A | 12/1993 | Funkenbusch et al. |
| 5,279,742 | A | 1/1994 | Markell et al. |
| 5,284,940 | A | 2/1994 | Lin et al. |
| 5,294,668 | A | 3/1994 | Babu |
| 5,328,758 | A | 7/1994 | Markell et al. |
| 5,334,316 | A | 8/1994 | Bruening et al. |
| 5,344,701 | A | 9/1994 | Gagnon et al. |
| 5,346,619 | A | 9/1994 | Funkenbusch et al. |
| 5,349,125 | A | 9/1994 | Holton et al. |
| 5,376,528 | A | 12/1994 | King et al. |
| 5,380,901 | A | 1/1995 | Antonucci et al. |
| RE34,910 | E | 4/1995 | Funkenbusch et al. |
| 5,405,951 | A | 4/1995 | Woodard |
| 5,415,779 | A | 5/1995 | Markell et al. |
| 5,438,127 | A | 8/1995 | Woodard et al. |
| 5,438,128 | A | 8/1995 | Nieuwkerk et al. |
| 5,438,129 | A | 8/1995 | Woodard et al. |
| 5,451,453 | A | 9/1995 | Gagnon et al. |
| 5,464,541 | A | 11/1995 | Aysta et al. |
| 5,472,600 | A | 12/1995 | Ellefson et al. |
| 5,486,358 | A | 1/1996 | Coleman et al. |
| 5,510,084 | A | 4/1996 | Cros et al. |
| 5,512,439 | A | 4/1996 | Hornes et al. |
| 5,525,319 | A | 6/1996 | Woodard et al. |
| 5,543,305 | A | 8/1996 | Cummins et al. |
| 5,585,236 | A | 12/1996 | Bonn et al. |
| 5,595,649 | A | 1/1997 | Markell et al. |
| 5,610,287 | A | 3/1997 | Nikiforov et al. |
| 5,620,663 | A | 4/1997 | Aysta et al. |
| 5,620,852 | A | 4/1997 | Lin et al. |
| 5,625,053 | A | 4/1997 | Kresheck et al. |
| 5,633,290 | A | 5/1997 | Frechet et al. |
| 5,635,060 | A | 6/1997 | Hagen et al. |
| 5,637,687 | A | 6/1997 | Wiggins |
| 5,639,372 | A | 6/1997 | Hagen et al. |
| 5,639,599 | A | 6/1997 | Ryder et al. |
| 5,688,370 | A | 11/1997 | Hagen et al. |
| 5,691,208 | A | 11/1997 | Miltenyi et al. |
| 5,702,610 | A | 12/1997 | Hagen et al. |
| 5,709,943 | A | 1/1998 | Coleman et al. |
| 5,738,790 | A | 4/1998 | Hagen et al. |
| 5,741,828 | A | 4/1998 | Stoy et al. |
| 5,786,208 | A | 7/1998 | Clark et al. |
| 5,786,219 | A | 7/1998 | Zhang et al. |
| 5,801,237 | A | 9/1998 | Johansson |
| 5,804,684 | A | 9/1998 | Su |
| 5,834,583 | A | 11/1998 | Hancock et al. |
| 5,856,379 | A | 1/1999 | Shiratsuchi et al. |
| 5,869,002 | A | 2/1999 | Limon et al. |
| 5,882,521 | A | 3/1999 | Bouvier et al. |
| 5,904,848 | A | 5/1999 | Wong et al. |
| 5,919,626 | A | 7/1999 | Shi et al. |
| 5,976,367 | A | 11/1999 | Bouvier et al. |
| 5,976,468 | A | 11/1999 | Godec et al. |
| 5,993,935 | A | 11/1999 | Rasmussen et al. |
| 5,997,818 | A | 12/1999 | Hacker et al. |
| 5,999,935 | A | 12/1999 | Clark et al. |
| 6,007,690 | A | 12/1999 | Nelson et al. |
| 6,048,457 | A | 4/2000 | Kopaciewicz et al. |
| 6,048,550 | A | 4/2000 | Chan et al. |
| 6,063,589 | A | 5/2000 | Kellogg et al. |
| 6,063,838 | A | 5/2000 | Patnode et al. |
| 6,068,751 | A | 5/2000 | Neukermans |
| 6,071,406 | A | 6/2000 | Tsou |
| 6,074,827 | A | 6/2000 | Nelson et al. |
| 6,074,927 | A | 6/2000 | Kepler et al. |
| 6,084,091 | A | 7/2000 | Muller et al. |
| 6,093,558 | A | 7/2000 | Seed et al. |
| 6,093,559 | A | 7/2000 | Bookbinder et al. |
| RE36,811 | E | 8/2000 | Markell et al. |
| 6,103,199 | A | 8/2000 | Bjornson et al. |
| 6,143,247 | A | 11/2000 | Sheppard, Jr. et al. |
| 6,143,248 | A | 11/2000 | Kellogg et al. |
| 6,168,948 | B1 | 1/2001 | Anderson et al. |
| 6,197,595 | B1 | 3/2001 | Anderson et al. |
| 6,200,474 | B1 | 3/2001 | Kopaciewicz et al. |
| 6,207,251 | B1 | 3/2001 | Balsimo et al. |
| 6,254,780 | B1 | 7/2001 | Bouvier et al. |
| 6,261,497 | B1 | 7/2001 | Wong et al. |
| 6,265,168 | B1 | 7/2001 | Gjerde et al. |
| 6,265,224 | B1 | 7/2001 | Collis |
| 6,277,488 | B1 | 8/2001 | Kobe et al. |
| 6,284,113 | B1 | 9/2001 | Bjornson et al. |
| 6,302,134 | B1 | 10/2001 | Kellogg et al. |
| 6,306,273 | B1 | 10/2001 | Wainright et al. |
| 6,319,469 | B1 | 11/2001 | Mian et al. |
| 6,344,326 | B1 | 2/2002 | Nelson et al. |
| 6,348,336 | B1 | 2/2002 | Matveld et al. |
| 6,383,783 | B1 | 5/2002 | Haddad |
| 6,428,707 | B1 | 8/2002 | Berg et al. |
| 6,440,725 | B1 | 8/2002 | Pourahmadi et al. |
| 6,450,047 | B2 | 9/2002 | Swedberg et al. |
| 6,451,260 | B1 | 9/2002 | Düsterhoft et al. |
| 6,465,225 | B1 | 10/2002 | Fuhr et al. |
| 6,479,300 | B1 | 11/2002 | Jiang et al. |
| 6,504,021 | B2 | 1/2003 | Kristyanne et al. |
| 6,527,432 | B2 | 3/2003 | Kellogg et al. |
| 6,532,997 | B1 | 3/2003 | Bedingham et al. |
| 6,537,502 | B1 | 3/2003 | Shukla et al. |
| 6,544,734 | B1 | 4/2003 | Briscoe et al. |
| 6,548,788 | B2 | 4/2003 | Kellogg et al. |
| 6,582,662 | B1 | 6/2003 | Kellogg et al. |
| 6,617,136 | B2 | 9/2003 | Parthasarathy et al. |
| 6,627,159 | B1 | 9/2003 | Bedingham et al. |
| 6,632,399 | B1 | 10/2003 | Kellogg et al. |
| 6,664,104 | B2 | 12/2003 | Pourahmadi et al. |
| 6,664,354 | B2 | 12/2003 | Savu et al. |
| 6,692,596 | B2 | 2/2004 | Moll et al. |
| 6,720,187 | B2 | 4/2004 | Bedingham et al. |
| 6,723,236 | B2 | 4/2004 | Fisk et al. |
| 6,730,516 | B2 | 5/2004 | Jedrzejewski et al. |
| 6,734,401 | B2 | 5/2004 | Bedingham et al. |
| 6,780,818 | B2 | 8/2004 | Gundel et al. |
| 6,790,642 | B2 | 9/2004 | Haddad |
| 6,814,935 | B2 | 11/2004 | Harms et al. |
| 6,833,238 | B2 | 12/2004 | Ramstad et al. |
| 6,852,781 | B2 | 2/2005 | Savu et al. |

| | | | | |
|---|---|---|---|---|
| 6,875,348 | B2 | 4/2005 | Zare et al. | |
| 6,919,058 | B2 | 7/2005 | Andersson et al. | |
| 6,998,271 | B2 | 2/2006 | Wong et al. | |
| 7,026,168 | B2 | 4/2006 | Bedingham et al. | |
| 7,033,747 | B2 | 4/2006 | Gordon | |
| 7,138,436 | B2 | 11/2006 | Tan et al. | |
| 7,189,368 | B2 | 3/2007 | Andersson et al. | |
| 7,192,560 | B2 | 3/2007 | Parthasarathy et al. | |
| 7,214,348 | B2 | 5/2007 | Desmond et al. | |
| 7,311,880 | B2 | 12/2007 | Perman et al. | |
| 7,322,254 | B2 | 1/2008 | Bedingham et al. | |
| 7,347,976 | B2 | 3/2008 | Parthasarathy et al. | |
| 7,374,724 | B2 | 5/2008 | Ingenhoven et al. | |
| 7,662,340 | B2 | 2/2010 | Nagaoka | |
| 2001/0045000 | A1 | 11/2001 | Gundel et al. | |
| 2002/0001848 | A1 | 1/2002 | Bedingham et al. | |
| 2002/0046966 | A1 | 4/2002 | Muscate-Magnussen | |
| 2002/0047003 | A1 | 4/2002 | Bedingham et al. | |
| 2002/0048533 | A1 | 4/2002 | Harms et al. | |
| 2002/0064885 | A1 | 5/2002 | Bedingham et al. | |
| 2002/0155034 | A1 | 10/2002 | Perman et al. | |
| 2002/0182114 | A1 | 12/2002 | Ingenhoven et al. | |
| 2003/0011092 | A1 | 1/2003 | Tan et al. | |
| 2003/0013203 | A1 | 1/2003 | Jedrzejewski et al. | |
| 2003/0017551 | A1 | 1/2003 | Parthasarathy et al. | |
| 2003/0017567 | A1 | 1/2003 | Parthasarathy et al. | |
| 2003/0018177 | A1 | 1/2003 | Haddad | |
| 2003/0044322 | A1 | 3/2003 | Andersson et al. | |
| 2003/0053934 | A1 | 3/2003 | Andersson et al. | |
| 2003/0062310 | A1 | 4/2003 | Zare et al. | |
| 2003/0120062 | A1 | 6/2003 | Parthasarathy et al. | |
| 2003/0138779 | A1 | 7/2003 | Parthasarathy et al. | |
| 2003/0139549 | A1 | 7/2003 | Savu et al. | |
| 2003/0139550 | A1 | 7/2003 | Savu et al. | |
| 2003/0152491 | A1 | 8/2003 | Kellogg et al. | |
| 2003/0155034 | A1 | 8/2003 | De Beukeleer et al. | |
| 2003/0228701 | A1 | 12/2003 | Wong et al. | |
| 2003/0228706 | A1 | 12/2003 | Ramstad et al. | |
| 2004/0016702 | A1 | 1/2004 | Hennessy et al. | |
| 2004/0018116 | A1 | 1/2004 | Desmond et al. | |
| 2004/0018559 | A1 | 1/2004 | Lau et al. | |
| 2004/0171170 | A1 * | 9/2004 | Sandell | 436/180 |
| 2004/0209258 | A1 | 10/2004 | Parthasarathy et al. | |
| 2005/0126312 | A1 | 6/2005 | Bedingham et al. | |
| 2005/0130177 | A1 | 6/2005 | Bedingham et al. | |
| 2005/0142563 | A1 | 6/2005 | Haddad et al. | |
| 2005/0142570 | A1 | 6/2005 | Parthasarathy et al. | |
| 2005/0142571 | A1 | 6/2005 | Parthasarathy et al. | |
| 2005/0142663 | A1 | 6/2005 | Parthasarathy et al. | |
| 2006/0013732 | A1 | 1/2006 | Parthasarathy et al. | |
| 2007/0160504 | A1 | 7/2007 | Parthasarathy et al. | |

FOREIGN PATENT DOCUMENTS

| | | | |
|---|---|---|---|
| EP | 0 281 368 | | 9/1988 |
| EP | 0 309 259 | A2 | 3/1989 |
| EP | 0 309 259 | A3 | 3/1989 |
| EP | 0 389 063 | A2 | 9/1990 |
| EP | 0 389 063 | A3 | 9/1990 |
| EP | 0 409 432 | A2 | 1/1991 |
| EP | 0 409 432 | A3 | 1/1991 |
| EP | 0 426 488 | A1 | 5/1991 |
| EP | 0 447 362 | A1 | 9/1991 |
| EP | 0 572 907 | A2 | 12/1993 |
| EP | 0 572 907 | A3 | 12/1993 |
| EP | 0 309 259 | B1 | 6/1994 |
| EP | 0 426 488 | B1 | 4/1997 |
| EP | 0 770 689 | A2 | 5/1997 |
| EP | 0 389 063 | B1 | 8/1997 |
| EP | 0 524 864 | | 5/1998 |
| EP | 0 897 978 | A2 | 2/1999 |
| EP | 0 897 978 | A3 | 2/1999 |
| JP | 2 268 682 | | 11/1990 |
| JP | 2 295 485 | | 12/1990 |
| JP | 7 265 718 | | 10/1995 |
| JP | 9 302 034 | | 11/1997 |
| WO | WO 90/10637 | | 9/1990 |
| WO | WO 92/16659 | | 10/1992 |
| WO | WO 92/18514 | | 10/1992 |
| WO | WO 94/00464 | | 1/1994 |
| WO | WO 95/19781 | | 7/1995 |
| WO | WO 95/24505 | | 9/1995 |
| WO | WO 97/21090 | | 6/1997 |
| WO | WO 97/27325 | | 7/1997 |
| WO | WO 98/04909 | | 2/1998 |
| WO | WO 98/12351 | | 3/1998 |
| WO | WO 98/39094 | | 9/1998 |
| WO | WO 99/15876 | | 4/1999 |
| WO | WO 99/15888 | | 4/1999 |
| WO | WO 99/22021 | | 5/1999 |
| WO | WO 99/23487 | | 5/1999 |
| WO | WO 99/28504 | | 6/1999 |
| WO | WO 99/39120 | | 8/1999 |
| WO | WO 99/40174 | | 8/1999 |
| WO | WO 99/46591 | | 9/1999 |
| WO | WO 99/58664 | | 11/1999 |
| WO | WO 00/45180 | | 8/2000 |
| WO | WO 00/62051 | | 10/2000 |
| WO | WO 00/68336 | | 11/2000 |
| WO | WO 01/03149 | | 1/2001 |
| WO | WO 01/12327 | | 2/2001 |
| WO | WO 01/21632 | | 3/2001 |
| WO | WO 01/25490 | | 4/2001 |
| WO | WO 01/25491 | | 4/2001 |
| WO | WO 01/30873 | | 5/2001 |
| WO | WO 01/30995 | | 5/2001 |
| WO | WO 01/37291 | | 5/2001 |
| WO | WO 01/38516 | | 5/2001 |
| WO | WO 01/38865 | | 5/2001 |
| WO | WO 01/62976 | | 8/2001 |
| WO | WO 01/68240 | | 9/2001 |
| WO | WO 01/68913 | | 9/2001 |
| WO | WO 01/71732 | | 9/2001 |
| WO | WO 02/00347 | * | 1/2002 |
| WO | WO 02/44400 | | 6/2002 |
| WO | WO 03/054509 | | 7/2003 |
| WO | WO 03/054510 | | 7/2003 |
| WO | WO 03/058224 | | 7/2003 |
| WO | WO 2004/009851 | | 1/2004 |
| WO | WO 2004/010760 | | 2/2004 |
| WO | WO 2004/011141 | | 2/2004 |
| WO | WO 2004/011142 | | 2/2004 |
| WO | WO 2004/011592 | | 2/2004 |
| WO | WO 2004/011681 | | 2/2004 |
| WO | WO 2004/094672 | | 11/2004 |
| WO | WO 2005/005045 | | 1/2005 |

OTHER PUBLICATIONS

3M Material Safety Data Sheet for FC-4430 FLUORADJ Fluorosurfactant (9 pgs) (May 7, 2003).

3M Material Safety Data Sheet for 3M FLUORADJ Fluorosurfactant FC-4432 (9 pgs) (May 21, 2003).

__ABI Prism7 BigDyeJ Terminators v3.0 Cycle Sequencing Kit,__ product information [online]. Applied Biosystems, 2000, 2001 [retrieved Dec. 3, 2001]. Retrieved from the Internet: <URL:http://www.appliedbiosystems.com/products/productdetail.cfm?id=81>, p. 1.

Al-Soud et al., "Purification and Characterization of PCT-inhibitory Components in Blood Cells," *Journal of Clinical Microbiology*; vol. 39(2); pp. 485-493 (2001).

Altschuler et al., "Benchmarks: Plasmid DNA Isolation Utilizing a Novel Nonionic Detergent," *Biotechniques*; vol. 17(3):434, 436 (1994).

American Society of Testing Materials, "ASTM D 570-98, Standard Test Method for Water Absorption of Plastics," *Annual Book of ASTM Standards*, pp. 32-35, Publication page, and Title page (2003).

AutoSeq96 Dye Terminator Clean-up Kit / Adapter Plate for AutoSeq96, product catalogue [online]. Amersham Biosciences, 2001 [retrieved Dec. 3, 2001]. Retrieved from the Internet: <URL:http://www.apbiotech.com/stiboasp/showmodule.asp?nModuleid=164360>, pp. 1-2.

Bartl et al., "Simple and Broadly Applicable Preparation by Use of Magnetic Glass Particles," *Clin Chem Lab Med.*, vol. 36(8):557-559 (1998).

Behzadbehbahani et al., "Detection of BK Virus in Urine by Polymerase Chain Reaction: A Comparison of DNA Extraction Methods," Journal of Virological Methods, 1997, vol. 67:161-166.

"Blast," National Institutes of Health [online] United States, [retrieved Oct. 23, 2000]. Retrieved from the Internet:<URL:http://www.ncbi.nlm.nih.gov/BLAST>, 2 pgs.

Bischoff et la., "Isolation of Specific tRNAs Using an Ionic-Hydrophobic Mixed-Mode Chromatographic Matrix," *Analytical Biochemistry*, vol. 151: 526-533 (1985).

QIAmp DNA Blood Mini Kit Handbook, 28 pages (Jan. 2004).

Buffone et al., "*Isolation of DNA from Biological Specimens without Extraction with Phenol," Clin. Chem*., vol. 31, pp. 164-165 (1985).

Burckhardt, "*Amplification of DNA From Whole Blood," PCR Methods and Applications*, Cold Spring Harbor Laboratory Press, p. 239 (1994).

Cornett., "Cellular Lysis of *Streptococcus faeclis* Induced with Triton X-100," *Journal of Bacteriology*, Jul. 1978, vol. 135(1):153-160.

Emmer et al., "Wall deactivation with fluorosurfactants for capillary electrophoresis analysis of biomolecules," Electrophoresis, vol. 22(4), Feb. 2001, pp. 660-665, XP002325650, ISSN: 0173-0835, p. 664.

Daugherty, "Using ion Exchange Chromatography to Separate Proteins," Access Excellence Activities Exchange at the National Health Museum, Washington, D.C., 2007. Available online [retrieved Apr. 17, 2007]. Retrieved from the Internet: <http://www.accessexcellence.org/AE/AEC/AEF/1994/daugherty_ion.html>; 4 pgs.

Daughton, "Quantitaion of Acrylimide (and Polyacrylimide): Critical Review of Methods for Trace Determination/Formulation Analysis & Future-research Recommendations," Finaly Report No. CDG-02/88. Prepared for the California Public Health Foundation: Berkeley, CA. Jun. 23, 1988. Title page and table of contents only, 5 pgs.

Fraker et al., *Biochem. Biophys. Res. Commun*., vol. 80:849-857 (1978).

Garcia et al., "Comparison of Two Leukocyte Extraction Methods for Cytomegalovirus Antigenemia Assay," *Journal of Clinical Microbiology*, Jan. 1996, pp. 182-184.

Huber et al., "High-performance liquid chromatographic separation of detrilyated oligonucleotides on highly cross-linked poly-(styrene-divinylbenzene) particles," *Journal of Chromatography*; vol. 599: 113-118 (992).

Jeffreys et al., "*DNA 'Fingerprints' and Segragation Analysis of Multiple Markers in Human Pedigrees," Am. J. Hum. Genet*., vol. 39, pp. 11-24 (1986).

Kapustin et al., "Composite fluorine polymer-containing sorbents for isolation and purification of biopolymers," Bioorg. Khim., Nov. 1998, 24(11):868-876 (Abstract Only).

Kogan et al., "*An Improved Method for Prenatal Diagnosis of Genetic Diseases by Analysis of Amplified DNA Sequences, Application to Hemophilia A," New England Journal of Medicine*, vol. 317, pp. 985-990 (1987).

Kroschwitz et al., (Eds.); Kirk-Othmer Encyclopedia of Chemical Technology, $4^{th}$ Ed . . . , John Wiley and Sons; NY; vol. 23: 506-523 (1997).

Kube et al., "Quantitive DNA slot blot analysis: inhibition of DNA binding to membranes by magnesium ions," Nucleic Acids Research, 1997; 25(16):3375-3376.

Nielsen et al., "*Peptide nucleic acid (PNA), a DNA mimic with a pseudopeptide backbone," Chem. Soc. Rev*., vol. 26, pp. 73-78 (1997).

Rudbeck et al., "Benchmarks: Rapid, Simple Alkaline Extraction of Human Genomic DNA from Whole Blood, Buccal Epithelial Cells, Semen, and Forensic Stains for PCR," *Biotechniques*, vol. 25(4): 588-589, 592 (1998).

Tian et al., "Evaluation of Silica Resins for Direct and Efficient Extraction of DNA from Complex Biological Matrices in a Minaturized Format," Analyitical Biochemistry, vol. 283:175-191 (2000).

"Porex Corporate Profile," [online]. Porex Corporation, 2001 [retrieved Dec. 5, 2001]. Retrieved from the Internet: <URL:http://www.porex.com/english/corporate/index.asp>, pp. 1-3.

"Porex Products Group," product profile [online]. Porex Corporation, 2001 [retrieved Dec. 5, 2001]. Retrieved from the Internet: <URL:http://www.porex.com/english/porous/index.asp>, pp. 1-2.

Product Information Brochure, "DuPont Zonyl Fluoroadditives for Coatings Technical Information," (4 pgs) (Mar. 2003).

Product Information Brochure, "3M Novec Fluorosurfactants FC-4430/ 3M Fluorad Fluorosurfactants are now 3M Novec Fluorosurfactants," (4 pgs) (Oct. 2003).

Product Information Brochure, "Zonyl Fluorosurfactants," (2 pgs), obtained from the internet on Dec. 1, 2003, <URL:http://web.singnet.com.sg/~paseded/dupont6.htm>.

Product Information "Purification so fast it'll make your head spin: RapTract Dye Terminator Removal Kit," Prolinx Product Information, Bothell, WA, 2000. pp. 1-6.

"3M Empore Products 96-Well Plates," product listing [online]. 3M Corporation, 1999 [retrieved Dec. 5, 2001]. Retrieved from the Internet: <URL:http://www.mmm.com/empore/formats/Plates/sorbavlb/index.htm>, pp. 1-2.

"3M Empore Products Empore 96-Well Plates" SPE Extraction Disk Plates & Filter Plates, 3M Extraction Disk Plates for SPE, product listing [online]. 3M Corporation, 1999 [retrieved Dec. 5, 2001]. Retrieved from the Internet: <URL:http://www.mmm.com/empore/formats/Plates/index.htm>, pp. 1-2.

Takeuchi et al., "Ion Chromatography Using Anion Exchangers Modified with Anionic Polysaccharides," LCGC Magazine [online]. LCGC North America, 2001 [retrieved Oct. 2, 2001]. Retrieved from the Internet: <URL:http://www.lcgcmag.com/articles/0004_articles/0004_Takeuchi/0004_Takeuchi.asp>, pp. 1-12.

Tong et al., "Solid-Phase Method for the Purification of DNA Sequencing Reactions," *Anal Chem*, 1992; vol. 64, No. 22; pp. 2672-2677, Publication page, and Title page.

Villee, "Biology," Seventh Edition, W.B. Saunders Company, Philadelphia, PA, 1977; Title Page, Publication page and p. 877 (3 pgs).

Yamaguchi et al., "Increased Sensitivity for Detection of Human Cytomegalovirus in Urine by Removal of Inhibitors for the Polymerase Chain Reaction," *Journal of Virological Methods*, 1992, vol. 37(2):209-218.

Boom et al., "Rapid and Simple Method for Purification of Nucleic Acids," *Journal of Clinical Microbiology*, Mar. 1990, vol. 28, No. 3; pp. 495-503, Publication page and Title page.

Breadmore et al., "Microchip-Based Purification of DNA from Biological Samples," *Analytical Chemistry*; vol. 75(8):1880-1886 (2003).

Brezinski et al., "Laying the foundation for New Technologies 3M Creates a new building block for its fluorosurfactants," *Paintings and Coatings Industry* (Jan. 2003).

Kroschwitz et al., (Eds.); Kirk-Othmer Encyclopedia of Chemical Technology, $4^{th}$ Ed . . . , John Wiley and Sons; NY; vol. 23: 506-523 (1997).

* cited by examiner

VARIABLE VALVE APPARATUS AND METHODS

CROSS-REFERENCE TO RELATED APPLICATIONS

This is a Continuation of U.S. patent application Ser. No. 11/684,656, filed Mar. 12, 2007, now abandoned which is a Continuation of U.S. patent application Ser. No. 10/852,642, filed on May 24, 2004, now abandoned, which is a Continuation-In-Part of U.S. patent application Ser. No. 10/734,717, filed on Dec. 12, 2003, now U.S. Pat. No. 7,322,254 and claims priority to U.S. Provisional Patent Application Ser. No. 60/532,523, filed on Dec. 24, 2003, all of which are incorporated herein by reference in their entireties.

BACKGROUND

Sample processing devices including process chambers in which various chemical or biological processes are performed play an increasing role in scientific and/or diagnostic investigations. The process chambers provided in such devices are preferably small in volume to reduce the amount of sample material required to perform the processes.

One persistent issue associated with sample processing devices including process chambers is in the transfer of fluids between different features in the devices. Conventional approaches to separate and transfer fluidic contents of process chambers have often required human intervention (e.g., manual pipetting) and/or robotic manipulation. Such transfer processes suffer from a number of disadvantages including, but not limited to, the potential for errors, complexity and associated high costs, etc.

Attempts to address the fluid transfer issues have focused on transferring the entire fluid contents of the process chambers through, e.g., valves, tortuous paths, etc.

SUMMARY OF THE INVENTION

The present invention provides sample processing devices with valve structures. The valve structures allow for removal of selected portions of the sample material located within the process chamber. Removal of the selected portions is achieved by forming an opening in a valve septum at a desired location.

The valve septums are preferably large enough to allow for adjustment of the location of the opening based on the characteristics of the sample material in the process chamber. If the sample processing device is rotated after the opening is formed, the selected portion of the material located closer to the axis of rotation exits the process chamber through the opening. The remainder of the sample material cannot exit through the opening because it is located farther from the axis of rotation than the opening.

The openings in the valve septum may be formed at locations based on one or more characteristics of the sample material detected within the process chamber. It may be preferred that the process chambers include detection windows that transmit light into and/or out of the process chamber. Detected characteristics of the sample material may include, e.g., the free surface of the sample material (indicative of the volume of sample material in the process chamber). Forming an opening in the valve septum at a selected distance radially outward of the free surface can provide the ability to remove a selected volume of the sample material from the process chamber.

For sample materials that can be separated into various components, e.g., whole blood, rotation of the sample processing device may result in separation of the plasma and red blood cell components, thus allowing for selective removal of the components to, e.g., different process chambers.

In some embodiments, it may be possible to remove selected aliquots of the sample material by forming openings at selected locations in one or more valve septums. The selected aliquot volume can be determined based on the radial distance between the openings (measured relative to the axis of rotation) and the cross-sectional area of the process chamber between the opening.

The openings in the valve septums are preferably formed in the absence of physical contact, e.g., through laser ablation, focused optical heating, etc. As a result, the openings can preferably be formed without piercing the outermost layers of the sample processing device, thus limiting the possibility of leakage of the sample material from the sample processing device.

In one aspect, the present invention provides a valved process chamber on a sample processing device, the valved process chamber including a process chamber having a process chamber volume located between opposing first and second major sides of the sample processing device, wherein the process chamber occupies a process chamber area on the sample processing device, and wherein the process chamber area has a length and a width transverse to the length, and further wherein the length is greater than the width. The valved process chamber also includes a valve chamber located within the process chamber area, the valve chamber located between the process chamber volume and the second major side of the sample processing device, wherein the valve chamber is isolated from the process chamber by a valve septum separating the valve chamber and the process chamber, and wherein a portion of the process chamber volume lies between the valve septum and a first major side of the sample processing device. A detection window is located within the process chamber area, wherein the detection window is transmissive to selected electromagnetic energy directed into and/or out of the process chamber volume.

In another aspect, the present invention provides a valved process chamber on a sample processing device, the valved process chamber including a process chamber having a process chamber volume located between opposing first and second major sides of the sample processing device, wherein the process chamber occupies a process chamber area on the sample processing device, and wherein the process chamber area has a length and a width transverse to the length, and further wherein the length is greater than the width. The valved process chamber also includes a valve chamber located within the process chamber area, the valve chamber located between the process chamber volume and the second major side of the sample processing device, wherein the valve chamber is isolated from the process chamber by a valve septum separating the valve chamber and the process chamber, and wherein a portion of the process chamber volume lies between the valve septum and a first major side of the sample processing device, and further wherein the valve chamber and the detection window occupy mutually exclusive portions of the process chamber area, and still further wherein at least a portion of the valve chamber is located within a valve lip extending into the process chamber area, and wherein the valve septum is formed in the valve lip. A detection window is located within the process chamber area, wherein the detection window is transmissive to selected electromagnetic energy directed into and/or out of the process chamber volume.

In another aspect, the present invention includes a method of selectively removing sample material from a process chamber. The method includes providing a sample processing device that includes a process chamber having a process chamber volume, wherein the process chamber occupies a process chamber area on the sample processing device; a valve chamber located within the process chamber area, wherein the valve chamber is isolated from the process chamber by a valve septum located between the valve chamber and the process chamber; and a detection window located within the process chamber area, wherein the detection window is transmissive for selected electromagnetic energy. The method further includes providing sample material in the process chamber; detecting a characteristic of the sample material in the process chamber through the detection window; and forming an opening in the valve septum at a selected location along the length of the process chamber, wherein the selected location is correlated to the detected characteristic of the sample material. The method also includes moving only a portion of the sample material from the process chamber into the valve chamber through the opening formed in the valve septum.

In another aspect, the present invention provides a method of selectively removing sample material from a process chamber. The method includes providing a sample processing device having a process chamber with a process chamber volume, wherein the process chamber occupies a process chamber area on the sample processing device, and wherein the process chamber area includes a length and a width transverse to the length, and further wherein the length is greater than the width. The sample processing device also includes a valve chamber located within the process chamber area, wherein the valve chamber is isolated from the process chamber by a valve septum located between the valve chamber and the process chamber; and a detection window located within the process chamber area, wherein the detection window is transmissive for selected electromagnetic energy. The method also includes providing sample material in the process chamber; detecting a characteristic of the sample material in the process chamber through the detection window; forming an opening in the valve septum at a selected location within the process chamber area, wherein the selected location is correlated to the detected characteristic of the sample material; and moving only a portion of the sample material from the process chamber into the valve chamber through the opening formed in the valve septum by rotating the sample processing device.

In another embodiment, the present invention provides a method of isolating nucleic acid from whole blood, the method including: providing a device that includes a loading chamber and a variable valved process chamber; placing whole blood in the loading chamber; transferring the whole blood to a valved process chamber; centrifuging the whole blood in the valved process chamber to form a plasma layer (often the upper layer), a red blood cell layer (often the lower layer), and an interfacial layer that includes white blood cells; removing at least a portion of the interfacial layer; and lysing the white blood cells in the separated interfacial layer and optionally lysing the nuclei therein to release inhibitors and/or nucleic acid.

If desired, prior to lysing the white blood cells, the method can include diluting the separated interfacial layer of the sample with water (preferably, RNAse-free sterile water) or buffer, optionally further concentrating the diluted layer to increase the concentration of nucleic acid material, optionally separating the further concentrated region, and optionally repeating this process of dilution followed by concentration and separation to reduce the inhibitor concentration to that which would not interfere with an amplification method.

Alternatively, before, simultaneously with, or after lysing the white blood cells, if desired, the method can include transferring the separated interfacial layer to a separation chamber for contact with solid phase material to preferentially adhere at least a portion of the inhibitors to the solid phase material; wherein the solid phase material includes capture sites (e.g., chelating functional groups), a coating reagent coated on the solid phase material, or both; wherein the coating reagent is selected from the group consisting of a surfactant, a strong base, a polyelectrolyte, a selectively permeable polymeric barrier, and combinations thereof.

Another embodiment of the present invention involves a method of isolating nucleic acid from whole blood using a density gradient material. In this embodiment, the method includes: providing a device that includes a loading chamber and a variable valved process chamber; placing whole blood in the loading chamber; transferring the whole blood to a valved process chamber; contacting the whole blood with a density gradient material; centrifuging the whole blood and density gradient material in the valved process chamber to form layers, at least one of which contains cells of interest; removing at least a portion of the layer that includes the cells of interest; and lysing the separated cells of interest to release nucleic acid.

In another embodiment, the present invention provides a method of isolating nucleic acid from whole blood that includes a pathogen, the method includes: providing a device that includes a loading chamber, a variable valved process chamber, and a separation chamber with pathogen capture material therein; placing whole blood in the loading chamber; transferring the whole blood to a valved process chamber; centrifuging the whole blood in the valved process chamber to form a plasma layer that includes a pathogen, a red blood cell layer, and an interfacial layer that includes white blood cells; transferring at least a portion of the plasma layer with the pathogen to the separation chamber including pathogen capture material; separating at least a portion of the pathogen from the pathogen capture material; and lysing the pathogen to release nucleic acid.

The present invention also provides kits for carrying out the various methods of the present invention.

These and other features and advantages of the present invention are described below in connection with various illustrative embodiments of the devices and methods of the present invention.

DEFINITIONS

"Nucleic acid" shall have the meaning known in the art and refers to DNA (e.g., genomic DNA, cDNA, or plasmid DNA), RNA (e.g., mRNA, tRNA, or rRNA), and PNA. It can be in a wide variety of forms, including, without limitation, double-stranded or single-stranded configurations, circular form, plasmids, relatively short oligonucleotides, peptide nucleic acids also called PNA's (as described in Nielsen et al., *Chem. Soc. Rev.*, 26, 73-78 (1997)), and the like. The nucleic acid can be genomic DNA, which can include an entire chromosome or a portion of a chromosome. The DNA can include coding (e.g., for coding mRNA, tRNA, and/or rRNA) and/or non-coding sequences (e.g., centromeres, telomeres, intergenic regions, introns, transposons, and/or microsatellite sequences). The nucleic acid can include any of the naturally occurring nucleotides as well as artificial or chemically modified nucleotides, mutated nucleotides, etc. The nucleic acid can include a non-nucleic acid component, e.g., peptides (as in PNA's), labels (radioactive isotopes or fluorescent markers), and the like.

"Nucleic acid-containing material" refers to a source of nucleic acid such as a cell (e.g., white blood cell, enucleated red blood cell), a nuclei, or a virus, or any other composition that houses a structure that includes nucleic acid (e.g., plasmid, cosmid, or viroid, archeobacteriae). The cells can be prokaryotic (e.g., gram positive or gram negative bacteria) or eukaryotic (e.g., blood cell or tissue cell). If the nucleic acid-containing material is a virus, it can include an RNA or a DNA genome; it can be virulent, attenuated, or noninfectious; and it can infect prokaryotic or eukaryotic cells. The nucleic acid-containing material can be naturally occurring, artificially modified, or artificially created.

"Isolated" refers to nucleic acid (or nucleic acid-containing material) that has been separated from at least a portion of the inhibitors (i.e., at least a portion of at least one type of inhibitor) in a sample. This includes separating desired nucleic acid from other materials, e.g., cellular components such as proteins, lipids, salts, and other inhibitors. More preferably, the isolated nucleic acid is substantially purified. "Substantially purified" refers to isolating nucleic acid of at least 3 picogram per microliter (pg/μL), preferably at least 2 nanogram/microliter (ng/μL), and more preferably at least 15 ng/μL, while reducing the inhibitor amount from the original sample by at least 20%, preferably by at least 80% and more preferably by at least 99%. The contaminants are typically cellular components and nuclear components such as heme and related products (hemin, hematin) and metal ions, proteins, lipids, salts, etc., other than the solvent in the sample. Thus, the term "substantially purified" generally refers to separation of a majority of inhibitors (e.g., heme and it degradation products) from the sample, so that compounds capable of interfering with the subsequent use of the isolated nucleic acid are at least partially removed.

"Adheres to" or "adherence" or "binding" refer to reversible retention of inhibitors to an optional solid phase material via a wide variety of mechanisms, including weak forces such as Van der Waals interactions, electrostatic interactions, affinity binding, or physical trapping. The use of this term does not imply a mechanism of action, and includes adsorptive and absorptive mechanisms.

"Solid phase material" (which can optionally be included within a device in methods of the present invention) refers to an inorganic and/or organic material, preferably a polymer made of repeating units, which may be the same or different, of organic and/or inorganic compounds of natural and/or synthetic origin. This includes homopolymers and heteropolymers (e.g., copolymers, terpolymers, tetrapolymers, etc., which may be random or block, for example). This term includes fibrous or particulate forms of a polymer, which can be readily prepared by methods well-known in the art. Such materials typically form a porous matrix, although for certain embodiments, the solid phase also refers to a solid surface, such as a nonporous sheet of polymeric material.

The optional solid phase material may include capture sites. "Capture sites" refer to sites on the solid phase material to which a material adheres. Typically, the capture sites include functional groups or molecules that are either covalently attached or otherwise attached (e.g., hydrophobically attached) to the solid phase material.

The phrase "coating reagent coated on the solid phase material" refers to a material coated on at least a portion of the solid phase material, e.g., on at least a portion of the fibril matrix and/or sorptive particles.

"Surfactant" refers to a substance that lowers the surface or interfacial tension of the medium in which it is dissolved.

"Strong base" refers to a base that is completely dissociated in water, e.g., NaOH.

"Polyelectrolyte" refers to an electrolyte that is a charged polymer, typically of relatively high molecular weight, e.g., polystyrene sulfonic acid.

"Selectively permeable polymeric barrier" refers to a polymeric barrier that allows for selective transport of a fluid based on size and charge.

"Concentrated region" refers to a region of a sample that has a higher concentration of nucleic acid-containing material, nuclei, and/or nucleic acid, which can be in a pellet form, relative to the less concentrated region.

"Substantially separating" as used herein, particularly in the context of separating a concentrated region of a sample from a less concentrated region of a sample, means removing at least 40% of the total amount of nucleic acid (whether it be free, within nuclei, or within other nucleic acid-containing material) in less than 25% of the total volume of the sample. Preferably, at least 75% of the total amount of nucleic acid in less than 10% of the total volume of sample is separated from the remainder of the sample. More preferably, at least 95% of the total amount of nucleic acid in less than 5% of the total volume of sample is separated from the remainder of the sample.

"Inhibitors" refer to inhibitors of enzymes used in amplification reactions, for example. Examples of such inhibitors typically include iron ions or salts thereof (e.g., $Fe^{2+}$ or salts thereof) and other metal salts (e.g., alkali metal ions, transition metal ions). Other inhibitors can include proteins, peptides, lipids, carbohydrates, heme and its degradation products, urea, bile acids, humic acids, polysaccharides, cell membranes, and cytosolic components. The major inhibitors in human blood for PCR are hemoglobin, lactoferrin, and IgG, which are present in erythrocytes, leukocytes, and plasma, respectively. The methods of the present invention separate at least a portion of the inhibitors (i.e., at least a portion of at least one type of inhibitor) from nucleic acid-containing material. As discussed herein, cells containing inhibitors can be the same as the cells containing nuclei or other nucleic acid-containing material. Inhibitors can be contained in cells or be extracellular. Extracellular inhibitors include all inhibitors not contained within cells, which includes those inhibitors present in serum or viruses, for example.

"Preferentially adhere at least a portion of the inhibitors to the solid phase material" means that one or more types of inhibitors will adhere to the optional solid phase material to a greater extent than nucleic acid-containing material (e.g., nuclei) and/or nucleic acid, and typically without adhering a substantial portion of the nucleic acid-containing material and/or nuclei to the solid phase material.

"Microfluidic" (where used herein) refers to a device with one or more fluid passages, chambers, or conduits that have at least one internal cross-sectional dimension, e.g., depth, width, length, diameter, etc., that is less than 500 μm, and typically between 0.1 μm and 500 μm. In the devices used in the present invention, the microscale channels or chambers may preferably have at least one cross-sectional dimension between 0.1 μm and 200 μm, more preferably between 0.1 μm and 100 μm, and often between 1 μm and 20 μm. Typically, a microfluidic device includes a plurality of chambers (process chambers, separation chambers, mixing chambers, waste chambers, diluting reagent chambers, amplification reaction chambers, loading chambers, and the like), each of the chambers defining a volume for containing a sample; and at least one distribution channel connecting the plurality of chambers of the array; wherein at least one of the chambers within the array can include a solid phase material (thereby often being referred to as a separation chamber) and/or at least one of the process chambers within the array can include a lysing reagent (thereby often being referred to as a mixing chamber), for example.

The terms "comprises" and variations thereof do not have a limiting meaning where these terms appear in the description and claims.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list. Furthermore, various embodiments are described in which the various elements of each embodiment could be used in other embodiments, even though not specifically described.

DETAILED DESCRIPTION OF ILLUSTRATIVE EMBODIMENTS OF THE INVENTION

Figure 1:
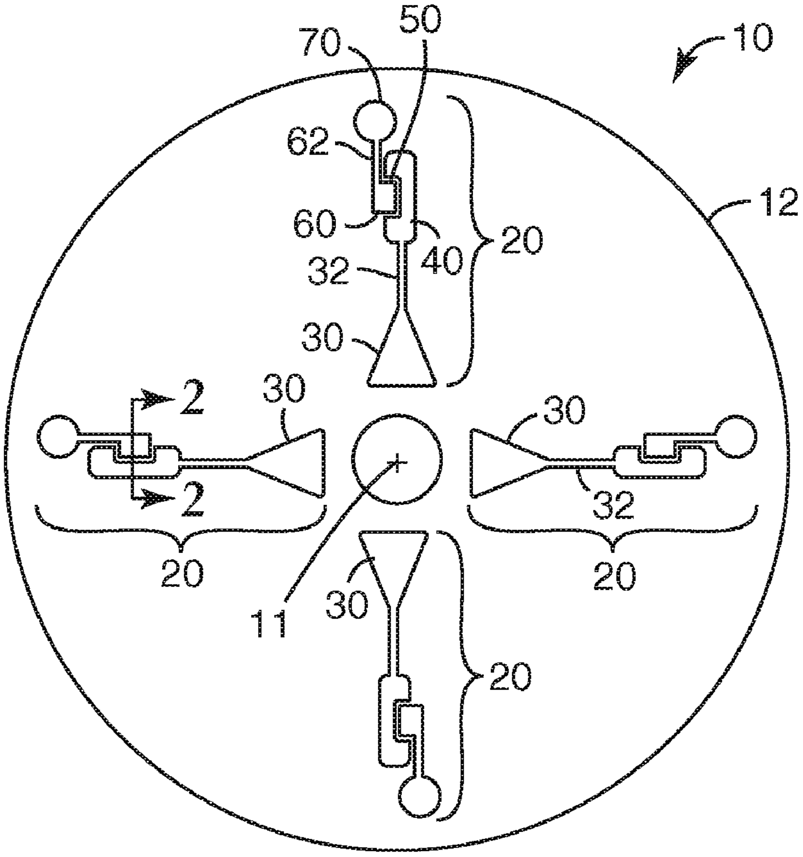
FIG. 1 is a plan view of one exemplary sample processing device according to the present invention.

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

The present invention provides a sample processing device that can be used in the processing of liquid sample materials (or sample materials entrained in a liquid) in multiple process chambers to obtain desired reactions, e.g., PCR amplification, ligase chain reaction (LCR), self-sustaining sequence replication, enzyme kinetic studies, homogeneous ligand binding assays, and other chemical, biochemical, or other reactions that may, e.g., require precise and/or rapid thermal variations. More particularly, the present invention provides sample processing devices that include one or more process arrays, each of which may preferably include a loading chamber, at least one process chamber, a valve chamber, and conduits for moving fluids between various components of the process arrays. The devices of the present invention may or may not include microfluidic features.

Although various constructions of illustrative embodiments are described below, sample processing devices of the present invention may be similar to those described in, e.g., U.S. Pat. Nos. 7,026,168 (Bedingham et al.); 6,814,935 (Bedingham et al.); 6,734,401 (Bedingham et al.), and 7,192,560 (Parthasarathy et al.); as well as U.S. Pat. No. 6,627,159 B1 (Bedingham et al.). The documents identified above all disclose a variety of different constructions of sample processing devices that could be used to manufacture sample processing devices according to the principles of the present invention.

Figure 2:
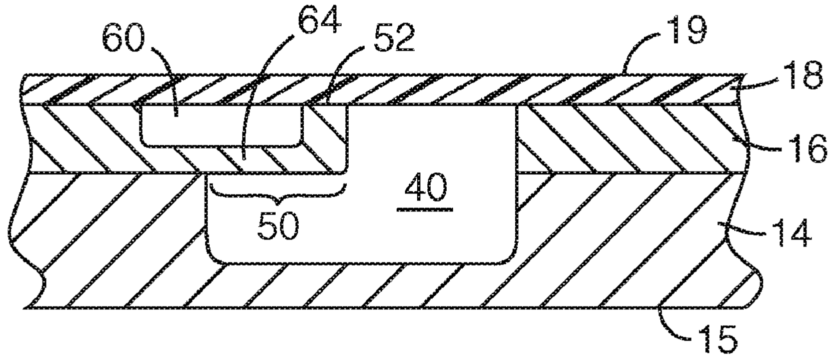
FIG. 2 is an enlarged cross-sectional view of a portion of the sample processing device of FIG. 1, taken along line 2-2 in FIG. 1.

One illustrative sample processing device manufactured according to the principles of the present invention is illustrated in FIGS. 1 & 2, where FIG. 1 is a plan view of one sample processing device 10 and FIG. 2 is an enlarged cross-sectional view of a portion of the sample processing device 10 (taken along line 2-2 in FIG. 1). The sample processing device 10 may preferably be in the shape of a circular disc as illustrated in FIG. 1, although any other shape that can be rotated could be used in place of a circular disc.

The sample processing device 10 includes at least one, and preferably multiple process arrays 20. If the sample processing device 10 is circular as depicted, it may be preferred that each of the depicted process arrays 20 extends from proximate a center 12 of the sample processing device 10 towards the periphery of the sample processing device 10. The process arrays 20 are depicted as being substantially aligned radially with respect to the center 12 of the sample processing device 10. Although this arrangement may be preferred, it will be understood that any arrangement of process arrays 20 may alternatively be used. Also, although the illustrated sample processing device 10 includes four process arrays 20, the exact number of process arrays provided in connection with a sample processing device manufactured according to the present invention may be greater than or less than four.

Each of the process arrays 20 (in the embodiment depicted in FIG. 1) includes a loading chamber 30 connected to a process chamber 40 along a conduit 32. The process arrays 20 also include a valve chamber 60 connected to a second process chamber 70 by a conduit 62. The valve chamber 60 may preferably be located within a valve lip 50 extending into the area occupied by the process chamber 40 on the sample processing device 10.

It should be understood that a number of the features associated with one or more of the process arrays 20 may be optional. For example, the loading chambers 30 and associated conduits 32 may be optional where sample material can be introduced directly into the process chambers 40 through a different loading structure. At the same time, additional features may be provided with one or more of the process arrays 20. For example, two or more valve chambers 60 may be associated with one or more of the process arrays 20. Additional valve chambers may be associated with additional process chambers or other features.

Any loading structure provided in connection with the process arrays 20 may be designed to mate with an external apparatus (e.g., a pipette, hollow syringe, or other fluid delivery apparatus) to receive the sample material. The loading structure itself may define a volume (as, e.g., does loading chamber 30 of FIG. 1) or the loading structure may define no specific volume, but, instead, be a location at which sample material is to be introduced. For example, the loading structure may be provided in the form of a port through which a pipette or needle is to be inserted. In one embodiment, the loading structure may be, e.g., a designated location along a conduit that is adapted to receive a pipette, syringe needle, etc. The loading may be performed manually or by an automated system (e.g., robotic, etc.). Further, the sample processing device 10 may be loaded directly from another device (using an automated system or manually).

FIG. 2 is an enlarged cross-sectional view of the processing device 10 taken along line 2-2 in FIG. 1. Although sample processing devices of the present invention may be manufactured using any number of suitable construction techniques, one illustrative construction can be seen in the cross-sectional view of FIG. 2. The sample processing device 10 includes a base layer 14 attached to a valve layer 16. A cover layer 18 is attached to the valve layer 16 over the side of the valve layer 16 that faces away from the base layer 14.

The layers of sample processing device 10 may be manufactured of any suitable material or combination of materials. Examples of some suitable materials for the base layer 14 and/or valve layer 16 include, but are not limited to, polymeric material, glass, silicon, quartz, ceramics, etc. For those sample processing devices 10 in which the layers will be in direct contact with the sample materials, it may be preferred that the material or materials used for the layers be non-reactive with the sample materials. Examples of some suitable polymeric materials that could be used for the substrate in many different bioanalytical applications may include, but are not limited to, polycarbonate, polypropylene (e.g., isotactic polypropylene), polyethylene, polyester, etc.

The layers making up sample processing device 10 may be attached to each other by any suitable technique or combination of techniques. Suitable attachment techniques preferably have sufficient integrity such that the attachment can withstand the forces experienced during processing of sample materials in the process chambers. Examples of some of the suitable attachment techniques may include, e.g., adhesive attachment (using pressure sensitive adhesives, curable adhesives, hot melt adhesives, etc.), heat sealing, thermal welding, ultrasonic welding, chemical welding, solvent bonding, coextrusion, extrusion casting, etc. and combinations thereof. Furthermore, the techniques used to attach the different layers may be the same or different. For example, the technique or techniques used to attach the base layer 14 and the valve layer 16 may be the same or different as the technique or techniques used to attach the cover layer 18 and the valve layer 16.

FIG. 2 depicts a process chamber 40 in its cross-sectional view. Also seen in FIG. 2 is the valve lip 50 that, in the depicted embodiment is located within the area occupied by the process chamber, i.e., the process chamber area. The process chamber are may preferably be defined by projecting the process chamber boundaries onto either of the major sides of the sample processing device 10. In the embodiment depicted in FIG. 2, a first major side 15 of the sample processing device 10 is defined by the lowermost surface of base layer 14 (i.e., the surface facing away from valve layer 16) and a second major side 19 is defined by the uppermost surface of cover layer 18 (i.e., the surface facing away from the valve layer 16). It should be understood that "upper" and "lower" as used herein are with reference to FIG. 2 only and are not to be construed as limiting the orientation of the sample processing device 10 in use.

The valve lip 50 is depicted as extending into the process chamber area as defined by the outermost boundaries of process chamber 40. Because the valve lip 50 is located within the process chamber area, the valve lip 50 may be described as overhanging a portion of the process chamber 40 or being cantilevered over a portion of the process chamber 40.

Preferred process chambers of the present invention may include a detection window that allows the detection of one or more characteristics of any sample material in the process chamber 40. It may be preferred that the detection be achieved using selected light, where the term "light" refers to electromagnetic energy, whether visible to the human eye or not. It may be preferred that the light fall within a range of ultraviolet to infrared electromagnetic energy, and, in some instances, it may be preferred that light include electromagnetic energy in the spectrum visible to the human eye. Furthermore, the selected light may be, e.g., light of one or more particular wavelengths, one or more ranges of wavelengths, one or more polarization states, or combinations thereof.

In the embodiment depicted in FIG. 2, the detection window may be provided in the cover layer 18 or in the base layer 14 (or both). Regardless of which component is used as the detection window, the materials used preferably transmit significant portions of selected light. For the purposes of the present invention, significant portions may be, e.g., 50% or more of normal incident selected light, more preferably 75% or more of normal incident selected light. Examples of some suitable materials for the detection window include, but are not limited to, e.g., polypropylenes, polyesters, polycarbonates, polyethylenes, polypropylene-polyethylene copolymers, cyclo-olefin polymers (e.g., polydicyclopentadiene), etc.

In some instances, it may be preferred that the base layer 14 and/or the cover layer 18 of the sample processing device 10 be opaque such that the sample processing device 10 is opaque between the volume of the process chamber volume 14 and at least one side of the sample processing device 10. By opaque, it is meant that transmission of the selected light as described above is substantially prevented (e.g., 5% or less of such normally incident light is transmitted).

Valve chamber 60 is depicted in FIG. 2 and may preferably be at least partially located within the valve lip 50 as seen in FIG. 2. At least a portion of the valve chamber 60 may preferably be located between the second major side 19 of the sample processing device 10 and at least a portion of the process chamber 40. The valve chamber 60 is also preferably isolated from the process chamber 40 by a valve septum 64 separating the valve chamber 64 and the process chamber 40, such that a portion of the volume of the process chamber 40 lies between the valve septum 64 and the first major side 15 of the sample processing device 10. In the depicted embodiment, the cover layer 18 is preferably sealed to the valve lip 50 along surface 52 to isolate the valve chamber 60 from the process chamber 50.

The valve septum 64 is preferably formed of material in which openings can be formed by non-contact methods, e.g., laser ablation, etc. As such the material or materials used in the septum 64 may include materials that preferentially absorb the energy used to open the septum 64. For example, the septum 64 may include materials such as, e.g., carbon black, UV/IR absorbers. etc.

The energy used to form openings in the valve septum 64 can be directed onto the valve septum 64 either through the cover layer 18 or through the base layer 14 (or through both). It may be preferred, however, that the energy be directed at the valve septum 64 through the cover layer 18 to avoid issues that may be associated with directing the energy through the sample material in the process chamber 40 before it reaches the valve septum 64.

One illustrative method of using a process array 120 will now be described with respect to FIGS. 3A-3D, each of which is a plan view of the process array in various stages of one illustrative method according to the present invention. The process array 120 depicted in each of the figures includes a loading chamber 130 connected to a process chamber 140 through conduit 132. The process array also includes a valve lip 150 and a valve chamber 160 located within a portion of the valve lip 150. The valve lip 150 and the valve chamber 160 define a valve septum 164 separating and isolating the valve chamber 160 from the process chamber 140 before any openings are formed through the valve septum 164. The valve septum 164 boundary is depicted as a broken line in the figures because it may not be visible to the naked eye.

Another feature of the process array 120 is a detection window 142 through selected light can be transmitted into and/or out of the process chamber 140. The detection window 142 may be formed through either major side of the device in which process array 120 is located (or through both major sides if so desired). In the depicted embodiment, the detection window 142 may preferably be defined by that portion of the area occupied by the process chamber 140 that is not also occupied by the valve lip 150. In another manner of characterizing the detection window 142, the detection window 142 and the valve lip 150 (and/or valve chamber 160 contained therein) may be described as occupying mutually exclusive portions of the area of the process chamber 140.

The process array 120 also includes an output process chamber 170 connected to the valve chamber 160 through conduit 162. The output process chamber 170 may include, e.g., one or more reagents 172 located therein. The reagent 172 may be fixed within the process chamber 170 or it may be loose within the process chamber. Although depicted in process chamber 170, one or more reagents may be provided at any suitable location or locations within the process array 120, e.g., the loading chamber 130, conduits 132 & 162, process chamber 140, valve chamber 160, etc.

The use of reagents is optional, i.e., sample processing devices of the present invention may or may not include any reagents in the process chambers. In another variation, some of the process chambers in different process arrays may include a reagent, while others do not. In yet another variation, different process chambers may contain different reagents. Further, the interior of the process chamber structures may be coated or otherwise processed to control the adhesion of reagents.

The process chamber 140 (and its associated process chamber area) may preferably have a length (measured along, e.g., axis 121 in FIG. 3A) that is greater than the width of the process chamber 140, where the process chamber width is measured perpendicular to the process chamber length. As such, the process chamber 140 may be described as "elongated." It may be preferred that the axis 121 along which the process chamber 140 is elongated be aligned with a radial direction extending from an axis of rotation about which the sample processing device containing process array is rotated (if rotation is the driving force used to effect fluid transfer).

In other aspects, it may be preferred that the detection window 142 be at least coextensive along the length of the process chamber 140 with the valve septum 164. Although the depicted detection window 142 is a single unitary feature, it will be understood that more two or more detection windows could be provided for each process chamber 140. For example, a plurality of independent detection windows could be distributed along the length of the process chamber 140 (e.g., alongside the valve septum 164.

Another manner of characterizing the relative sizes of the various features may be, e.g., that the valve septum 164 extends along the length of the process chamber area for 30% or more (or, alternatively, for 50% or more) of a maximum length of the process chamber 140 (along its elongation axis 121). Such a characterization of the dimensions of valve septum 164 may be expressed in actual measurements for many sample processing devices, e.g., the valve septum 164 may be described as extending for a length of 1 millimeter or more along the length of the process chamber 140.

Figure 3A:
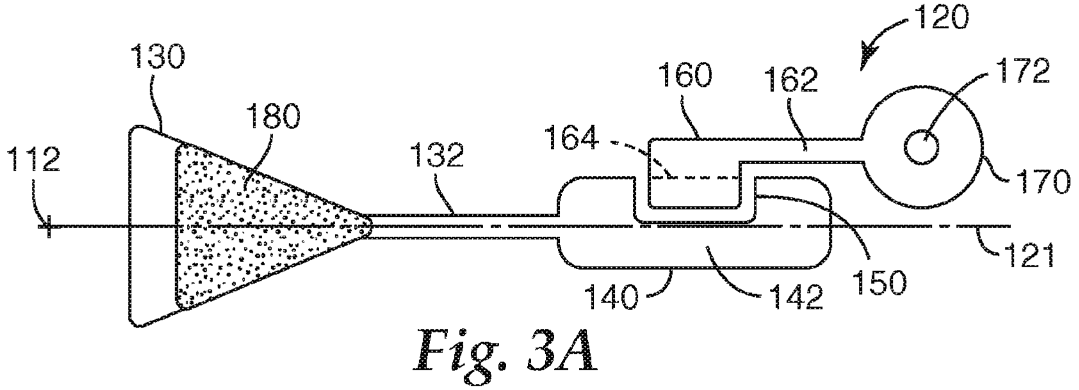
FIGS. 3A-3D depict one exemplary method of moving fluid through a process array including a process chamber and a valve chamber.

The first stage of the depicted method is seen in FIG. 3A, where the loading chamber 130 includes sample material 180 located therein. For the purposes of the illustrated method, the sample material 180 is whole blood. After loading, the blood 180 is preferably transferred to the process chamber 140 through conduit 132. The transfer may preferably be effected by rotating the process array 120 about an axis of rotation 111. The rotation may preferably occur, for example, in the plane of the paper on which FIG. 3A is located, although any rotation about point 111 in which process chamber 140 is moved in an arc about a point located on the opposite side of the loading chamber 130 from the process chamber 140 may be acceptable. A further description of a preferred process for processing whole blood to remove the nucleic acid is provided below.

The process arrays used in sample processing devices of the present invention may preferably be "unvented." As used in connection with the present invention, an "unvented process array" is a process array (i.e., at least two connected chambers) in which the only openings leading into the process array are located in the loading structure, e.g., the loading chamber. In other words, to reach the process chamber within an unvented process array, sample materials must be delivered to the loading chamber. Similarly, any air or other fluid located within the process array before loading of the sample material must also escape from the process array through the loading chamber. In contrast, a vented process array would include at least one opening outside of the loading chamber. That opening would allow for the escape of any air or other fluid located within the process array before loading.

Moving sample material through sample processing devices that include unvented process arrays may be facilitated by alternately accelerating and decelerating the device during rotation, essentially burping the sample materials through the conduits and process chambers. The rotating may be performed using at least two acceleration/deceleration cycles, i.e., an initial acceleration, followed by deceleration, second round of acceleration, and second round of deceleration. It may further be helpful if the acceleration and/or deceleration are rapid. The rotation may also preferably only be in one direction, i.e., it may not be necessary to reverse the direction of rotation during the loading process. Such a loading process allows sample materials to displace the air in those portions of the process arrays that are located farther from the center of rotation of the device. The actual acceleration and deceleration rates may vary based on a variety of factors such as temperature, size of the device, distance of the sample material from the axis of rotation, materials used to manufacture the devices, properties of the sample materials (e.g., viscosity), etc.

Figure 3B:
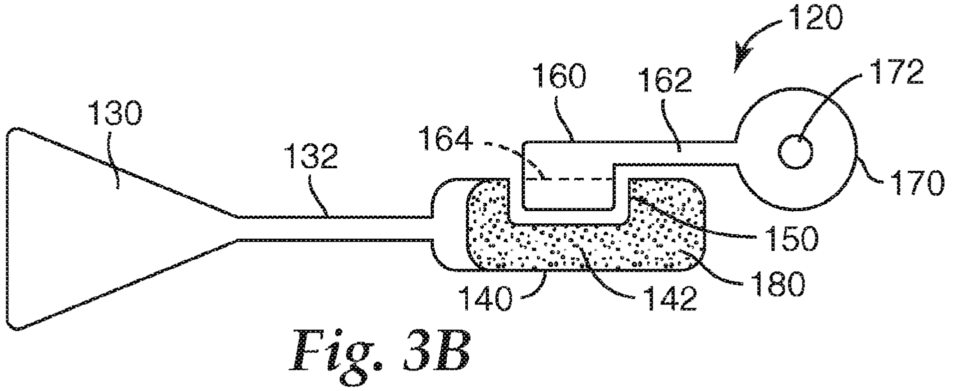

FIG. 3B depicts the process array after movement of the blood 180 into the process chamber 140. The blood 180 remains in the process chamber 140, i.e., does not travel into the valve chamber 160, because the valve chamber 160 is isolated from the process chamber 140 by the valve septum 164.

Figure 3C:
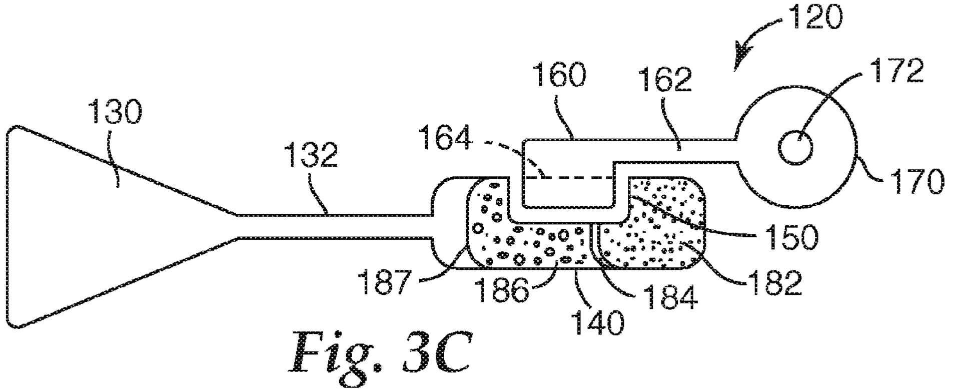
Figure 3D:
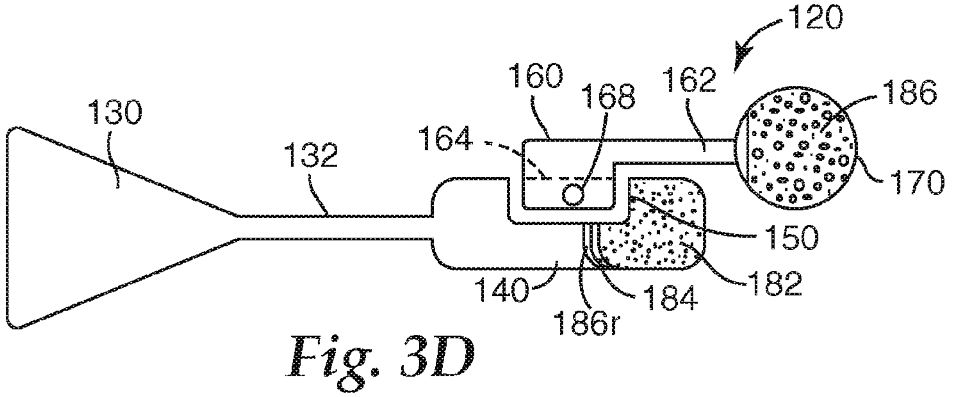

Additional rotation of the process array 120 may preferably result in separation of the components of the blood 180 into, as seen in FIG. 3C, red blood cells 182, a buffy coat layer 184, and plasma 186. The separation is typically a result of centrifugal forces and the relative densities of the materials.

If the precise volume of the different components in each sample of blood 180 (or if the volume of the blood sample 180 itself) is not known, the location of the boundaries between the different separated layers may not be known. In connection with the present invention, however, it may preferably be possible to detect the locations of the boundaries between the different separated components.

Such detection may preferably occur through the detection window using any suitable selected light. The light may be transmitted through or reflected from the blood components 182, 184 & 186 to obtain an image of the sample material in the process chamber 140. In another alternative, absorbance of light may be used to detect the boundaries or locations of one or more selected components. For example, after spinning blood, it may be possible to detect the interfaces between the packed red blood cell layer, the buffy layer (white blood cells), and plasma. After spinning beads, it may be possible to detect the interface between the packed bead layer and a supernatant layer.

It may be preferable to determine the location of all features or characteristics of the sample material, i.e., the location of all boundaries, including the free surface 187 of the plasma 186. In other instances, it may be sufficient to determine the location of only one feature, e.g., the boundary between the buffy coat layer 184 and the plasma 186, where the detected characteristic provides sufficient information to perform the next step in the method.

After the suitable characteristic or characteristics of the materials in the process chamber 140 have been detected, an opening 168 is preferably formed in the valve septum 164 at the desired location. In the depicted method, the desired location for opening 168 is chosen to remove a portion of the plasma 186 from the process chamber 140. It may be desirable that substantially all of the plasma 186 be removed, leaving only a small amount (see 186*r* in FIG. 3D) in the process chamber 140. It may be necessary to leave a small amount of plasma in the process chamber 140 to limit or prevent the transfer of red blood cells 182 out of the process chamber 140.

The opening 168 can be formed by any suitable non-contact technique. One such technique may be, e.g., laser ablation of the valve septum 168. Other techniques may include, but are not limited to, e.g., focused optical heating, etc.

After the opening 168 is formed, additional rotation of the process array 120 preferably moves the plasma 186 from the process chamber 140 into the valve chamber 160 through opening 168, followed by transfer into the output process chamber 170 through conduit 162. As a result, the plasma 186 is located in the process chamber 170, with a small remainder of plasma 186*r* in the process chamber 140 along with the buffy coat layer 184 and red blood cells 182.

Figure 4:
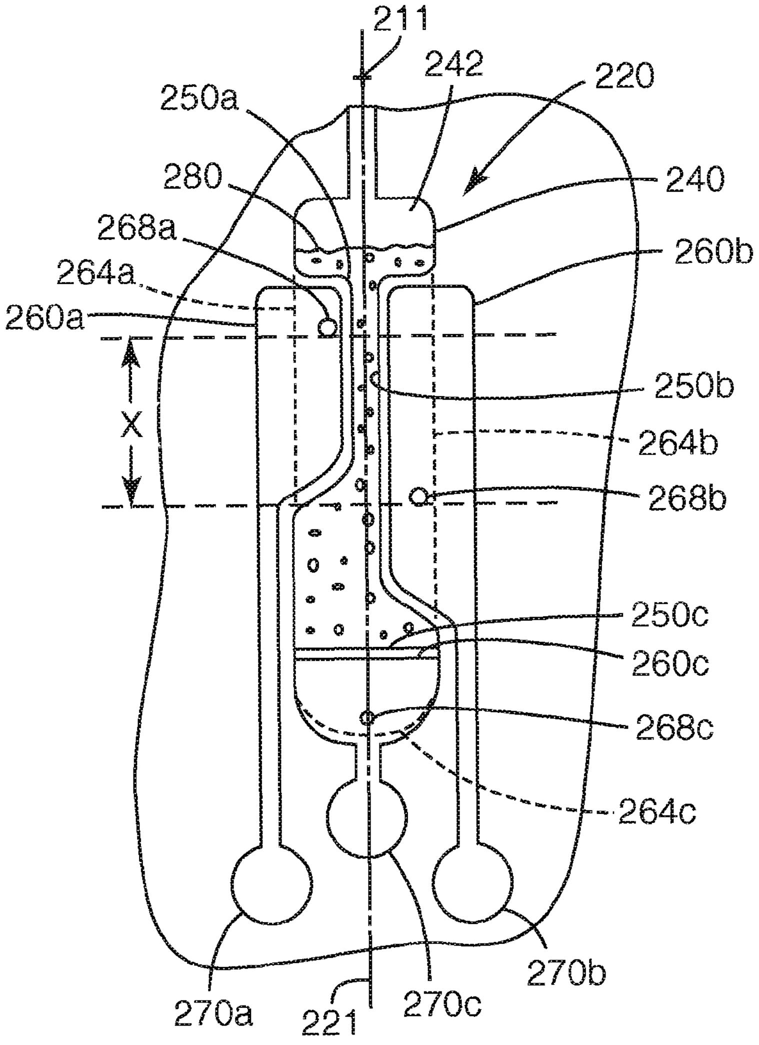
FIG. 4 is a plan view of an alternative process chamber and multiple valve chambers in accordance with the present invention.

A portion of another embodiment of a process array 220 including a process chamber 240 and valve structures according to the present invention is depicted in FIG. 4. In the depicted embodiment, the process chamber 240 is elongated along axis 221 and the process array 220 is designed for rotation to provide the force to move fluids. The rotation may be about point 211 which, in the depicted embodiment, lies on axis 221. It should, however, be understood that the point about which the process array is rotated is not required to lie on axis 221.

The process chamber 240 is shown in broken lines where the valve lips 250*a*, 250*b* and 250*c* extend into the process chamber area and in solid lines where the valve lips 250*a*, 250*b* and 250*c* do not extend into the process chamber area. It may be preferred that in those portions of the process chamber area that are not occupied by the valve lips 250*a*, 250*b* and 250*c*, the process chamber 240 include a detection window 242 that allows for the transmission of selected light into and/or out of the process chamber 240 to allow for detection of sample material 280 in the process chamber 240.

The process array 220 also includes valve chambers 260*a*, 260*b*, and 260*c* isolated and separated from the process chamber 240. The valve chambers 260*a*, 260*b*, and 260*c* are each in communication with a chamber 270*a*, 270*b*, and 270*c* (respectively). The valve chambers 260*a*, 260*b*, and 260*c* may be connected to their respective chambers 270*a*, 270*b*, and 270*c* by a conduit as shown in FIG. 4.

Each of the valve chambers 260*a*, 260*b*, and 260*c* may preferably be located, at least in part, on a valve lip 250*a*, 250*b* and 250*c* (respectively). Each of the valve chambers 260*a*, 260*b*, and 260*c* may also preferably be isolated and separated from the process chamber 240 by a valve septum 264*a*, 264*b*, and 264*c* located within each of the valve chambers 260*a*, 260*b*, and 260*c*. Each of the valve septums 264*a*, 264*b*, and 264*c* is defined, in part, by the broken lines of process chamber 240.

The multiple valve chambers 260*a*, 260*b*, and 260*c* provided in connection with the process chamber 240 may provide the ability to selectively remove different portions of any sample material in the process chamber and to move that sample material to different chambers 270*a*, 270*b*, and 270*c*. For example, a first portion of sample material 280 in the process chamber 240 may be moved into chamber 270*a* by forming an opening 268*a* in valve septum 264*a* of valve chamber 260*a*.

After moving the first portion of sample material 280 into chamber 270*a* through opening 268*a* in valve chamber 260*a*, another opening 268*b* may be provided in valve septum 264*b* of valve chamber 260*b* to move a second portion of the sample material 280 into chamber 270*b*. The second portion will typically include the sample material 280 located between openings 268*a* and 268*b*. The distance separating those two openings along the length of the process chamber 240 is indicated by x in FIG. 4. As a result, the volume of the second portion of sample material 280 can be determined if the cross-sectional area of the process chamber 240 (taken in a plane perpendicular to the axis 221) is known. As a result, it may be possible to move a known or selected volume of sample material into chamber 270*b* by forming openings 268*a* and 268*b* a selected distance apart from each other.

The process chamber 240 also includes a third valve chamber 260*c* located in a valve lip 250*c* at the end of the process chamber 240 farthest from the point 211 about which the process array 220 may be rotated. The valve lip 250*c* extends over the entire width of the process chamber 240 (in contrast to the valve lips 250*a* and 250*b* that extend over only a portion of the width of the process chamber 240).

Figure 5:
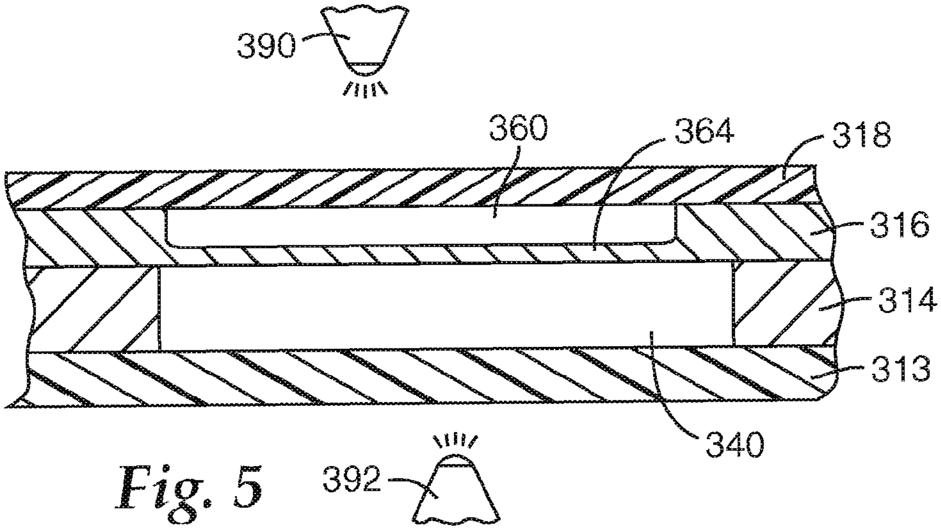
FIG. 5 is a cross-sectional view of another alternative process chamber and valve chamber construction according to the present invention, including optional detection apparatus facing both major sides of the sample processing device.

FIG. 5 depicts another process chamber 340 in connection with the present invention in cross-section. The process chamber 340 is formed in a sample processing device 310 that includes a base layer 313, intermediate layer 314, valve layer 316 and cover layer 318. The various layers may be attached to each other by any suitable combination of techniques.

Although the layers are depicted as single, homogeneous constructions, it will be understood that one or more of the layers could be formed of multiple materials and/or layers. Furthermore, it may be possible to combine some of the layers. For example, layers 313 and 314 may be combined (as an example, see layer 14 in the cross-sectional view of FIG. 2). Alternatively, it may be possible to combine layers 314 and 316 into a single structure that could be formed by, e.g., molding, extrusion, etc.

The construction seen in FIG. 5 includes a valve chamber 360 separated from the process chamber 340 by a valve septum 364. The valve chamber 360 is further defined by the cover layer 318. A device 390 is also depicted in FIG. 5 that can be used to, e.g., form an opening in the valve septum 364. The device 390 may be, e.g., a laser, etc. that can preferably deliver the energy necessary to form an opening in the valve septum 364 without forming an opening in the cover layer 318.

If the energy required to form openings in the valve septum 364 can be directed through the cover layer 318, then the base layer 313 may be formed of any material that may block such energy. For example, the base layer 313 may be made of, e.g., a metallic foil or other material. If the valve layer 316 and/or valve septum 364 allow for the passage of sufficient amounts of selected wavelengths of light, it may be possible to detect sample material in the process chamber 340 through the valve layer 316 and/or valve septum 364.

If, alternatively, the valve layer 316 and valve septum 364 block the passage of light such that detection of sample material in the process chamber 340 cannot be performed, then it may be desirable to detect sample material in the process chamber 340 through the base layer 313. Such detection may be accomplished using detection device 392 as seen in FIG. 5 that can detect sample material in the process chamber 340 through the layer 313. In some instances, it may be possible to form openings in the valve septum 364 using device 392 directing energy through layer 313 (if the passage of such energy through sample material in the process chamber 340 is acceptable).

Illustrative Method Using Whole Blood

The present invention also provides methods and kits for isolating nucleic acid from a whole blood that includes nucleic acid (e.g., DNA, RNA, PNA), which is included within nuclei-containing cells (e.g., white blood cells).

It should be understood that although the methods are directed to isolating nucleic acid from a sample, the methods do not necessarily remove the nucleic acid from the nucleic acid-containing material (e.g., nuclei). That is, further steps may be required to further separate the nucleic acid from the nuclei, for example.

Certain methods of the present invention may involve ultimately separating nucleic acid from inhibitors, such as heme and degradation products thereof (e.g., iron salts), which are undesirable because they can inhibit amplification reactions (e.g., as are used in PCR reactions). More specifically, certain methods of the present invention may involve separating at least a portion of the nucleic acid in a sample from at least a portion of at least one type of inhibitor. Preferred methods may involve removing substantially all the inhibitors in a sample containing nucleic acid such that the nucleic acid is substantially pure. For example, the final concentration of iron-containing inhibitors may preferably be no greater than about 0.8 micromolar (μM), which is the current level tolerated in conventional PCR systems.

In order to get clean DNA from whole blood, removal of hemoglobin as well as plasma proteins is typically desired. When red blood cells are lysed, heme and related compounds are released that inhibit Taq Polymerase. The normal hemoglobin concentration in whole blood is 15 grams (g) per 100 milliliters (mL) based on which the concentration of heme in hemolysed whole blood is around 10 millimolar (mM). For PCR to work out satisfactorily, the concentration of heme should be reduced to the micromolar (μM) level. This can be achieved, for example, by dilution or by removal of inhibitors using a material that binds inhibitors.

In one embodiment, the present invention provides a method of isolating nucleic acid from whole blood, the method includes: providing a device that includes a loading chamber and a variable valved process chamber; placing whole blood in the loading chamber; transferring the whole blood to a valved process chamber; centrifuging the whole blood in the valved process chamber to form a plasma layer (often the upper layer), a red blood cell layer (often the lower layer), and an interfacial layer (located between the plasma layer and the red blood cell layer) that includes white blood cells; removing at least a portion of the interfacial layer; and lysing the white blood cells in the separated interfacial layer and optionally lysing the nuclei therein to release inhibitors and/or nucleic acid. In certain embodiments, the lysing involves subjecting the white blood cells to a strong base with optional heating to release nucleic acid. If desired, the method can further include adjusting the pH of the sample that includes the released nucleic acid to be within a range of 7.5 to 9. Alternatively, the lysing can involve subjecting the white blood cells to a surfactant.

If desired, before, simultaneously with, or after lysing the white blood cells, the method can include transferring the separated interfacial layer to a separation chamber for contact with solid phase material to preferentially adhere at least a portion of the inhibitors to the solid phase material. More specifically, in certain embodiments of this method, the device further includes a separation chamber having a solid phase material therein. The solid phase material preferably includes capture sites (e.g., chelating functional groups), a coating reagent coated on the solid phase material, or both; wherein the coating reagent is selected from the group consisting of a surfactant, a strong base, a polyelectrolyte, a selectively permeable polymeric barrier, and combinations thereof.

When a solid phase material is present, the method includes contacting the lysed sample with the solid phase material in the separation chamber to preferentially adhere at least a portion of the inhibitors to the solid phase material; wherein lysing can occur before, simultaneous with, or after contacting the solid phase material. The method typically then includes separating at least a portion of the nuclei and/or nucleic acid from the solid phase material having at least a portion of the inhibitors adhered thereto.

In certain embodiments wherein no solid phase material is used, this method can involve diluting the lysed sample with water (preferably, RNAse-free sterile water) or buffer to reduce the inhibitor concentration to that which would not interfere with an amplification method; optionally further lysing the nuclei to release nucleic acid; optionally heating the sample to denature proteins and optionally adjusting the pH of the sample that includes released nucleic acid and optionally carrying out PCR. Diluting can be accomplished with sufficient water to reduce the concentration of heme to less than 2 micromolar. Alternatively, diluting can be accomplished with sufficient water to form a 2× to 1000× dilution of the lysed sample.

Alternatively, if desired, prior to lysing the white blood cells, the method can include diluting the separated interfacial layer of the sample with water or buffer, optionally further concentrating the diluted layer to increase the concentration of nucleic acid material, optionally separating the further concentrated region, and optionally repeating this process of dilution followed by concentration and separation to reduce the inhibitor concentration to that which would not interfere with an amplification method.

Figure 6:
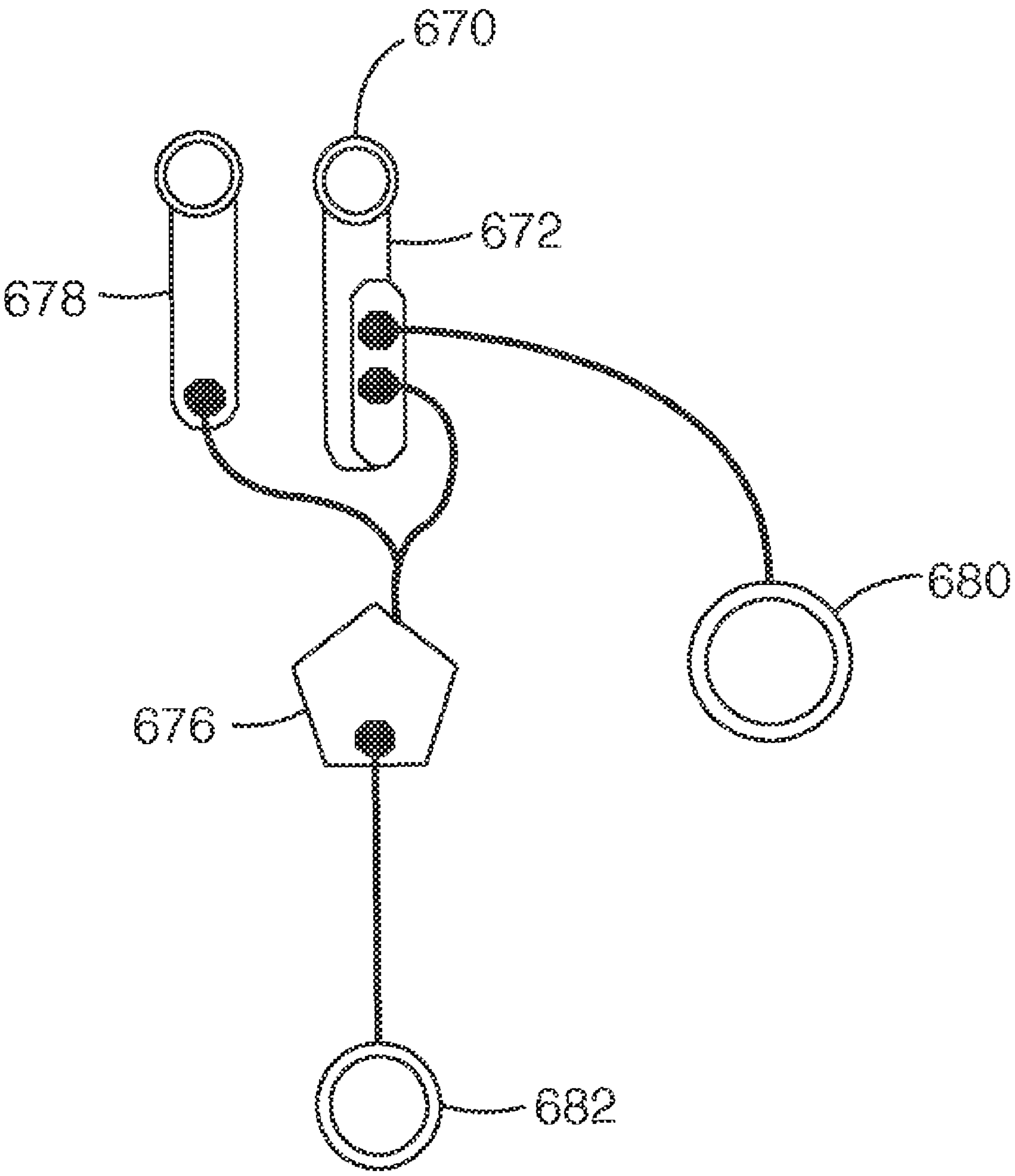
FIG. 6 is a representation of a device used in certain methods of the present invention.

Referring to FIG. 6, an example of one potentially preferred embodiment of the device suitable for use with these embodiments includes a loading chamber 670, a variable valved process chamber 672, an optional separation chamber 676, an eluting reagent chamber 678, a waste chamber 680, and an optional amplification chamber 682. These chambers are in fluid communication with each other such that a whole blood sample can be loaded into the loading chamber 670, which can then be transferred to the variable valved process chamber 672. Upon centrifuging the whole blood in the valved process chamber 672 to form a plasma layer (often the upper layer), a red blood cell layer (often the lower layer), and an interfacial layer that includes white blood cells, at least a portion (and preferably a substantial portion) of the interfacial layer is transferred to the optional separation chamber 676 to separate the white blood cells (buffy coat) from at least the red blood cell layer and preferably from both of the other two (the plasma layer and the red blood cell layer) layers of the whole blood, which can be transferred to the optional waste chamber 680. Therein the white blood cells in the buffy coat can be lysed to release inhibitors and nuclei and/or nucleic acid. If the separation chamber 676 includes a solid phase material, the process can include preferentially adhering at least a portion of the inhibitors to the solid phase material. The eluting reagent in the eluting reagent chamber 678 is then transferred to the separation chamber 676 to remove at least a portion of the target nucleic acid-containing material and/or nucleic acid. In certain embodiments, this material can be directly transferred to an amplification reaction chamber 682 for carrying out a PCR process, for example. The amplification reaction chamber 682 can optionally include pre-deposited reactants for the amplification reaction (e.g., PCR).

Lysing Reagents and Conditions

For certain embodiments of the invention, at some point during the process, cells within the sample, particularly nucleic acid-containing cells (e.g., white blood cells, bacterial cells, viral cells) are lysed to release the contents of the cells and form a sample (i.e., a lysate). Lysis, as used herein, is the physical disruption of the membranes of the cells, referring to the outer cell membrane and, when present, the nuclear membrane. This can be done using standard techniques, such as by hydrolyzing with proteinases followed by heat inactivation of proteinases, treating with surfactants (e.g., nonionic surfactants or sodium dodecyl sulfate), guanidinium salts, or strong bases (e.g., NaOH), disrupting physically (e.g., with ultrasonic waves), boiling, or heating/cooling (e.g., heating to at least 55° C. (typically to 95° C.) and cooling to room temperature or below (typically to 8° C.)), which can include a freezing/thawing process. Typically, if a lysing reagent is used, it is in aqueous media, although organic solvents can be used, if desired.

Lysing of red blood cells (RBC's) without the destruction of white blood cells (WBC's) in whole blood can occur to release inhibitors through the use of water (i.e., aqueous dilution) as the lysing agent (i.e., lysing reagent). Alternatively, ammonium chloride or quaternary ammonium salts can also be used to break RBC's. The RBC's can also be lysed by hypotonic shock with the use of a hypotonic buffer. The intact WBC's or their nuclei can be recovered by centrifugation, for example.

Typically, a stronger lysing reagent, such as a surfactant, can be used to lyse RBC's as well as nucleic acid-containing cells (e.g., white blood cells (WBC's), bacterial cells, viral cells) to release inhibitors, nuclei, and/or nucleic acid. For example, a nonionic surfactant can be used to lyse RBC's as well as WBC's while leaving the nuclei intact. Nonionic surfactants, cationic surfactants, anionic surfactants, and zwitterionic surfactants can be used to lyse cells. Particularly useful are nonionic surfactants. Combinations of surfactants can be used if desired. A nonionic surfactant such as TRITON X-100 can be added to a TRIS buffer containing sucrose and magnesium salts for isolation of nuclei.

The amount of surfactant used for lysing is sufficiently high to effectively lyse the sample, yet sufficiently low to avoid precipitation, for example. The concentration of surfactant used in lysing procedures is typically at least 0.1 wt-%, based on the total weight of the sample. The concentration of surfactant used in lysing procedures is typically no greater than 4.0 wt-%, and preferably, no greater than 1.0 wt-%, based on the total weight of the sample. The concentration is usually optimized in order to obtain complete lysis in the shortest possible time with the resulting mixture being PCR compatible. In fact, the nucleic acid in the formulation added to the PCR cocktail should allow for no inhibition of real-time PCR.

If desired, a buffer can be used in admixture with the surfactant. Typically, such buffers provide the sample with a pH of at least 7, and typically no more than 9.

Typically, an even stronger lysing reagent, such as a strong base, can be used to lyse any nuclei contained in the nucleic acid-containing cells (as in white blood cells) to release nucleic acid. For example, the method described in U.S. Pat. No. 5,620,852 (Lin et al.), which involves extraction of DNA from whole blood with alkaline treatment (e.g., NaOH) at room temperature in a time frame as short as 1 minute, can be adapted to certain methods of the present invention. Generally, a wide variety of strong bases can be used to create an effective pH (e.g., 8-13, preferably 13) in an alkaline lysis procedure. The strong base is typically a hydroxide such as NaOH, LiOH, KOH; hydroxides with quaternary nitrogen-containing cations (e.g., quaternary ammonium) as well as bases such as tertiary, secondary or primary amines. Typically, the concentration of the strong base is at least 0.01 Normal (N), and typically, no more than 1 N. Typically, the mixture can then be neutralized, particularly if the nucleic acid is to subjected to PCR. In another procedure, heating can be used subsequent to lysing with base to further denature proteins followed by neutralizing the sample.

One can also use Proteinase K with heat followed by heat inactivation of proteinase K at higher temperatures for isolation of nucleic acids from the nuclei or WBC.

One can also use a commercially available lysing agent and neutralization agent such as in Sigma's Extract-N-Amp Blood PCR kit scaled down to, e.g., microfluidic dimensions if desired. Stonger lysing solutions such as POWERLYSE from GenPoint (Oslo, Norway) for lysing difficult bacteria such as *Staphylococcus, Streptococcus*, etc. can be used to advantage in certain methods of the present invention.

In another procedure, a boiling method can be used to lyse cells and nuclei, release DNA, and precipitate hemoglobin simultaneously. The DNA in the supernatant can be used directly for PCR without a concentration step, making this procedure useful for low copy number samples.

For infectious diseases, it may be necessary to analyze bacterial or viruses from whole blood. For example, in the case of bacteria, white blood cells may be present in conjunction with bacterial cells. In a device, it would be possible to lyse red blood cells to release inhibitors, and then separate out bacterial cells and white blood cells by centrifugation, for example, prior to further lysing. This concentrated slug of nucleic acid-containing cells (bacterial and white blood cells/nuclei) can be moved further into a chamber for removal of inhibitors. Then, the bacterial cells, for example, can be lysed.

Bacterial cell lysis, depending on the type, may be accomplished using heat. Alternatively, bacterial cell lysis can occur using enzymatic methods (e.g., lysozyme, mutanolysin) or chemical methods. The bacterial cells are preferably lysed by alkaline lysis.

The use of bacteria for propagation of plasmids is common in the study of genomics, analytic molecular biology, preparatory molecular biology, etc. In the case of the bacterium containing plasmid, genetic material from both the bacterium and the plasmid are present. A clean-up procedure to separate cellular proteins and cellular fragments from genomic DNA can be carried out using a method of the present invention. The supernatant thus obtained, which contains the plasmid DNA, is called the "cleared lysate." The cleared lysate can be further purified using a variety of means, such as anion-exchange chromatography, gel filtration, or precipitation with alcohol.

In a specific example of a protocol for bacterial cultures, which can be incorporated into a device, an *E. Coli* cell culture is centrifuged and resuspended in TE buffer (10 mM TRIS, 1 mM EDTA, pH 7.5) and lysed by the addition of 0.1 M NaOH/1% SDS (sodium dodecyl sulfate). The cell lysis is stopped by the addition of 1 volume of 3 M (three molar) potassium acetate (pH 4.8) and the supernatant centrifuged. The cell lysate is further purified to get clean plasmid DNA.

Plasma and serum represent the majority of specimens submitted for molecular testing that include viruses. After fractionation of whole blood, plasma or serum samples can be used for the extraction of viruses (i.e., viral particles). For example, to isolate DNA from viruses, it may be possible to first separate out the serum by spinning blood. By the use of the variable valve, the serum alone can be emptied into another chamber. The serum can then be centrifuged to concentrate the virus or can be used directly in subsequent lysis steps after removal of the inhibitors using a solid phase material, for example, as described herein. The solid phase material could absorb the solution such that the virus particles do not go through the material. The virus particles can then be eluted out in a small elution volume. The virus can be lysed by heat or by enzymatic or chemical means, for example, by the use of surfactants, and used for downstream applications, such as PCR or real-time PCR. In cases where viral RNA is required, it may be necessary to have an RNAse inhibitor added to the solution to prevent degradation of RNA.

Optional Solid Phase Material

For certain embodiments of the invention, it has been found that inhibitors will adhere to solid phase materials that include a solid matrix in any form (e.g., particles, fibrils, a membrane), preferably with capture sites (e.g., chelating functional groups) attached thereto, a coating reagent (preferably, surfactant) coated on the solid phase material, or both. The coating reagent can be a cationic, anionic, nonionic, or zwitterionic surfactant. Alternatively, the coating reagent can be a polyelectrolyte or a strong base. Various combinations of coating reagents can be used if desired.

The solid phase material useful in the methods of the present invention may include a wide variety of organic and/or inorganic materials that retain inhibitors such as heme and heme degradation products, particularly iron ions, for example. Such materials are functionalized with capture sites (preferably, chelating groups), coated with one or more coating reagents (e.g., surfactants, polyelectrolytes, or strong bases), or both. Typically, the solid phase material includes an organic polymeric matrix.

Generally suitable materials are chemically inert, physically and chemically stable, and compatible with a variety of biological samples. Examples of solid phase materials include silica, zirconia, alumina beads, metal colloids such as gold, gold-coated sheets that have been functionalized through mercapto chemistry, for example, to generate capture sites. Examples of suitable polymers include for example, polyolefins and fluorinated polymers. The solid phase material is typically washed to remove salts and other contaminants prior to use. It can either be stored dry or in aqueous suspension ready for use. The solid phase material is preferably used in a flow-through receptacle, for example, such as a pipet, syringe, or larger column, microtiter plate, or other device, although suspension methods that do not involve such receptacles could also be used.

The solid phase material useful in the methods of the present invention can include a wide variety of materials in a wide variety of forms. For example, it can be in the form of particles or beads, which may be loose or immobilized, fibers, foams, frits, microporous film, membrane, or a substrate with microreplicated surface(s). If the solid phase material includes particles, they are preferably uniform, spherical, and rigid to ensure good fluid flow characteristics.

For flow-through applications of the present invention, such materials are typically in the form of a loose, porous network to allow uniform and unimpaired entry and exit of large molecules and to provide a large surface area. Preferably, for such applications, the solid phase material has a relatively high surface area, such as, for example, more than one meter squared per gram ($m^2/g$). For applications that do not involve the use of a flow-through device, the solid phase material may or may not be in a porous matrix. Thus, membranes can also be useful in certain methods of the present invention.

For applications that use particles or beads, they may be introduced to the sample or the sample introduced into a bed of particles/beads and removed therefrom by centrifuging, for example. Alternatively, particles/beads can be coated (e.g., pattern coated) onto an inert substrate (e.g., polycarbonate or polyethylene), optionally coated with an adhesive, by a variety of methods (e.g., spray drying). If desired, the substrate can be microreplicated for increased surface area and enhanced clean-up. It can also be pretreated with oxygen plasma, e-beam or ultraviolet radiation, heat, or a corona treatment process. This substrate can be used, for example, as a cover film, or laminated to a cover film, on a reservoir in a device.

In one embodiment, the solid phase material includes a fibril matrix, which may or may not have particles enmeshed therein. The fibril matrix can include any of a wide variety of fibers. Typically, the fibers are insoluble in an aqueous environment. Examples include glass fibers, polyolefin fibers, particularly polypropylene and polyethylene microfibers, aramid fibers, a fluorinated polymer, particularly, polytetrafluoroethylene fibers, and natural cellulosic fibers. Mixtures of fibers can be used, which may be active or inactive toward binding of nucleic acid. Preferably, the fibril matrix forms a web that is at least about 15 microns, and no greater than about 1 millimeter, and more preferably, no greater than about 500 microns thick.

If used, the particles are typically insoluble in an aqueous environment. They can be made of one material or a combination of materials, such as in a coated particle. They can be swellable or nonswellable, although they are preferably nonswellable in water and organic liquids. Preferably, if the particle is doing the adhering, it is made of nonswelling, hydrophobic material. They can be chosen for their affinity for the nucleic acid. Examples of some water swellable particles are described in U.S. Pat. Nos. 4,565,663 (Errede et al.), 4,460,642 (Errede et al.), and 4,373,519 (Errede et al.). Particles that are nonswellable in water are described in U.S. Pat. Nos. 4,810,381 (Hagen et al.), 4,906,378 (Hagen et al.), 4,971,736

(Hagen et al.); and 5,279,742 (Markell et al.). Preferred particles are polyolefin particles, such as polypropylene particles (e.g., powder). Mixtures of particles can be used, which may be active or inactive toward binding of nucleic acid.

If coated particles are used, the coating is preferably an aqueous- or organic-insoluble, nonswellable material. The coating may or may not be one to which nucleic acid will adhere. Thus, the base particle that is coated can be inorganic or organic. The base particles can include inorganic oxides such as silica, alumina, titania, zirconia, etc., to which are covalently bonded organic groups. For example, covalently bonded organic groups such as aliphatic groups of varying chain length (C2, C4, C8, or C18 groups) can be used.

Examples of suitable solid phase materials that include a fibril matrix are described in U.S. Pat. Nos. 5,279,742 (Markell et al.), 4,906,378 (Hagen et al.), 4,153,661 (Ree et al.), 5,071,610 (Hagen et al.), 5,147,539 (Hagen et al.), 5,207,915 (Hagen et al.), and 5,238,621 (Hagen et al.). Such materials are commercially available from 3M Company (St. Paul, Minn.) under the trade designations SDB-RPS (Styrene-Divinyl Benzene Reverse Phase Sulfonate, 3M Part No. 2241), cation-SR membrane (3M Part No. 2251), C-8 membrane (3M Part No. 2214), and anion-SR membrane (3M Part No. 2252).

Those that include a polytetrafluoroethylene matrix (PTFE) are particularly preferred. For example, U.S. Pat. No. 4,810,381 (Hagen et al.) discloses a solid phase material that includes: a polytetrafluoroethylene fibril matrix, and nonswellable sorptive particles enmeshed in the matrix, wherein the ratio of nonswellable sorptive particles to polytetrafluoroethylene being in the range of 19:1 to 4:1 by weight, and further wherein the composite solid phase material has a net surface energy in the range of 20 to 300 milliNewtons per meter. U.S. Pat. No. RE 36,811 (Markell et al.) discloses a solid phase extraction medium that includes: a PTFE fibril matrix, and sorptive particles enmeshed in the matrix, wherein the particles include more than 30 and up to 100 weight percent of porous organic particles, and less than 70 to 0 weight percent of porous (organic-coated or uncoated) inorganic particles, the ratio of sorptive particles to PTFE being in the range of 40:1 to 1:4 by weight.

Particularly preferred solid phase materials are available under the trade designation EMPORE from the 3M Company, St. Paul, Minn. The fundamental basis of the EMPORE technology is the ability to create a particle-loaded membrane, or disk, using any sorbent particle. The particles are tightly held together within an inert matrix of polytetrafluoroethylene (90% sorbent: 10% PTFE, by weight). The PTFE fibrils do not interfere with the activity of the particles in any way. The EMPORE membrane fabrication process results in a denser, more uniform extraction medium than can be achieved in a traditional Solid Phase Extraction (SPE) column or cartridge prepared with the same size particles.

In another preferred embodiment, the solid phase (e.g., a microporous thermoplastic polymeric support) has a microporous structure characterized by a multiplicity of spaced, randomly dispersed, nonuniform shaped, equiaxed particles of thermoplastic polymer connected by fibrils. Particles are spaced from one another to provide a network of micropores therebetween. Particles are connected to each other by fibrils, which radiate from each particle to the adjacent particles. Either, or both, the particles or fibrils may be hydrophobic. Examples of preferred such materials have a high surface area, often as high as 40 meters$^2$/gram as measured by Hg surface area techniques and pore sizes up to about 5 microns.

This type of fibrous material can be made by a preferred technique that involves the use of induced phase separation. This involves melt blending a thermoplastic polymer with an immiscible liquid at a temperature sufficient to form a homogeneous mixture, forming an article from the solution into the desired shape, cooling the shaped article so as to induce phase separation of the liquid and the polymer, and to ultimately solidify the polymer and remove a substantial portion of the liquid leaving a microporous polymer matrix. This method and the preferred materials are described in detail in U.S. Pat. Nos. 4,726,989 (Mrozinski), 4,957,943 (McAllister et al.), and 4,539,256 (Shipman). Such materials are referred to as thermally induced phase separation membranes (TIPS membranes) and are particularly preferred.

Other suitable solid phase materials include nonwoven materials as disclosed in U.S. Pat. No. 5,328,758 (Markell et al.). This material includes a compressed or fused particulate-containing nonwoven web (preferably blown microfibrous) that includes high sorptive-efficiency chromatographic grade particles.

Other suitable solid phase materials include those known as HIPE Foams, which are described, for example, in U.S. Pat. No. 7,138,436 (Tan et al.). "HIPE" or "high internal phase emulsion" means an emulsion that includes a continuous reactive phase, typically an oil phase, and a discontinuous or co-continuous phase immiscible with the oil phase, typically a water phase, wherein the immiscible phase includes at least 74 volume percent of the emulsion. Many polymeric foams made from HIPE's are typically relatively open-celled. This means that most or all of the cells are in unobstructed communication with adjoining cells. The cells in such substantially open-celled foam structures have intercellular windows that are typically large enough to permit fluid transfer from one cell to another within the foam structure.

The solid phase material can include capture sites for inhibitors. Herein, "capture sites" refer to groups that are either covalently attached (e.g., functional groups) or molecules that are noncovalently (e.g., hydrophobically) attached to the solid phase material.

Preferably, the solid phase material includes functional groups that capture the inhibitors. For example, the solid phase material may include chelating groups. In this context, "chelating groups" are those that are polydentate and capable of forming a chelation complex with a metal atom or ion (although the inhibitors may or may not be retained on the solid phase material through a chelation mechanism). The incorporation of chelating groups can be accomplished through a variety of techniques. For example, a nonwoven material can hold beads functionalized with chelating groups. Alternatively, the fibers of the nonwoven material can be directly functionalized with chelating groups.

Examples of chelating groups include, for example, $-(CH_2-C(O)OH)_2$, tris(2-aminoethyl)amine groups, iminodiacetic acid groups, nitrilotriacetic acid groups. The chelating groups can be incorporated into a solid phase material through a variety of techniques. They can be incorporated in by chemically synthesizing the material. Alternatively, a polymer containing the desired chelating groups can be coated (e.g., pattern coated) on an inert substrate (e.g., polycarbonate or polyethylene). If desired, the substrate can be microreplicated for increased surface area and enhanced clean-up. It can also be pretreated with oxygen plasma, e-beam or ultraviolet radiation, heat, or a corona treatment process. This substrate can be used, for example, as a cover film, or laminated to a cover film, on a reservoir in a device.

Chelating solid phase materials are commercially available and could be used as the solid phase material in the present invention. For example, for certain embodiments of the present invention, EMPORE membranes that include chelating groups such as iminodiacetic acid (in the form of the sodium salt) are preferred. Examples of such membranes are disclosed in U.S. Pat. No. 5,147,539 (Hagen et al.) and commercially available as EMPORE Extraction Disks (47 mm, No. 2271 or 90 mm, No. 2371) from the 3M Company. For certain embodiments of the present invention, ammonium-derivatized EMPORE membranes that include chelating groups are preferred. To put the disk in the ammonium form, it can be washed with 50 mL of 0.1M ammonium acetate buffer at pH 5.3 followed with several reagent water washes.

Examples of other chelating materials include, but are not limited to, crosslinked polystyrene beads available under the trade designation CHELEX from Bio-Rad Laboratories, Inc. (Hercules, Calif.), crosslinked agarose beads with tris(2-aminoethyl)amine, iminodiacetic acid, nitrilotriacetic acid, polyamines and polyimines as well as the chelating ion exchange resins commercially available under the trade designation DUOLITE C-467 and DUOLITE GT73 from Rohm and Haas (Philadelphia, Pa.), AMBERLITE IRC-748, DIAION CR11, DUOLITE C647.

Typically, a desired concentration density of chelating groups on the solid phase material is about 0.02 nanomole per millimeter squared, although it is believed that a wider range of concentration densities is possible.

Other types of capture materials include anion exchange materials, cation exchange materials, activated carbon, reverse phase, normal phase, styrene-divinyl benzene, alumina, silica, zirconia, and metal colloids. Examples of suitable anion exchange materials include strong anion exchangers such as quaternary ammonium, dimethylethanolamine, quaternary alkylamine, trimethylbenzyl ammonium, and dimethylethanolbenzyl ammonium usually in the chloride form, and weak anion exchangers such as polyamine. Examples of suitable cation exchange materials include strong cation exchangers such as sulfonic acid typically in the sodium form, and weak cation exchangers such as carboxylic acid typically in the hydrogen form. Examples of suitable carbon-based materials include EMPORE carbon materials, carbon beads, Examples of suitable reverse phase C8 and C18 materials include silica beads that are end-capped with octadecyl groups or octyl groups and EMPORE materials that have C8 and C18 silica beads (EMPORE materials are available from 3M Co., St. Paul, Minn.). Examples of normal phase materials include hydroxy groups and dihydroxy groups.

Commercially available materials can also be modified or directly used in methods of the present invention. For example, solid phase materials available under the trade designation LYSE AND GO (Pierce, Rockford, Ill.), RELEASE-IT (CPG, NJ), GENE FIZZ (Eurobio, France), GENE RELEASER (Bioventures Inc., Murfreesboro, Tenn.), and BUGS N BEADS (GenPoint, Oslo, Norway), as well as Zymo's beads (Zymo Research, Orange, Calif.) and Dynal's beads (Dynal, Oslo, Norway) can be incorporated into the methods of the present invention, particularly into a device as the solid phase capture material.

In certain embodiments of such methods, the solid phase material includes a coating reagent. The coating reagent is preferably selected from the group consisting of a surfactant, a strong base, a polyelectrolyte, a selectively permeable polymeric barrier, and combinations thereof. In certain embodiments of such methods, the solid phase material includes a polytetrafluoroethylene fibril matrix, sorptive particles enmeshed in the matrix, and a coating reagent coated on the solid phase material, wherein the coating reagent is selected from the group consisting of a surfactant, a strong base, a polyelectrolyte, a selectively permeable polymeric barrier, and combinations thereof. Herein, the phrase "coating reagent coated on the solid phase material" refers to a material coated on at least a portion of the solid phase material, e.g., on at least a portion of the fibril matrix and/or sorptive particles.

Examples of suitable surfactants are listed below.

Examples of suitable strong bases include NaOH, KOH, LiOH, $NH_4OH$, as well as primary, secondary, or tertiary amines.

Examples of suitable polyelectrolytes include, polystyrene sulfonic acid (e.g., poly(sodium 4-styrenesulfonate) or PSSA), polyvinyl phosphonic acid, polyvinyl boric acid, polyvinyl sulfonic acid, polyvinyl sulfuric acid, polystyrene phosphonic acid, polyacrylic acid, polymethacrylic acid, lignosulfonate, carrageenan, heparin, chondritin sulfate, and salts or other derivatives thereof.

Examples of suitable selectively permeable polymeric barriers include polymers such as acrylates, acryl amides, azlactones, polyvinyl alcohol, polyethylene imine, polysaccharides. Such polymers can be in a variety of forms. They can be water-soluble, water-swellable, water-insoluble, hydrogels, etc. For example, a polymeric barrier can be prepared such that it acts as a filter for larger particles such as white blood cells, nuclei, viruses, bacteria, as well as nucleic acids such as human genomic DNA and proteins. These surfaces could be tailored by one of skill in the art to separate on the basis of size and/or charge by appropriate selection of functional groups, by cross-linking, and the like. Such materials would be readily available or prepared by one of skill in the art.

Preferably, the solid phase material is coated with a surfactant without washing any surfactant excess away, although the other coating reagents can be rinsed away if desired. Typically, the coating can be carried out using a variety of methods such as dipping, rolling, spraying, etc. The coating reagent-loaded solid phase material is then typically dried, for example, in air, prior to use.

Particularly desirable are solid phase materials that are coated with a surfactant, preferably a nonionic surfactant. This can be accomplished according to the procedure set forth in the Examples Section. Although not intending to be limited by theory, the addition of the surfactant is believed to increase the wettability of the solid phase material, which allows the inhibitors to soak into the solid phase material and bind thereto.

The coating reagent for the solid phase materials are preferably aqueous-based solutions, although organic solvents (alcohols, etc.) can be used, if desired. The coating reagent loading should be sufficiently high such that the sample is able to wet out the solid phase material. It should not be so high, however, that there is significant elution of the coating reagent itself. Preferably, if the coating reagent is eluted with the nucleic acid, there is no more than about 2 wt-% coating reagent in the eluted sample. Typically, the coating solution concentrations can be as low as 0.1 wt-% coating reagent in the solution and as high as 10 wt-% coating reagent in the solution.

Surfactants

Nonionic Surfactants. A wide variety of suitable nonionic surfactants are known that can be used as a lysing reagent (discussed above), an eluting reagent (discussed below), and/or as a coating on the solid phase material. They include, for example, polyoxyethylene surfactants, carboxylic ester surfactants, carboxylic amide surfactants, etc. Commercially available nonionic surfactants include, n-dodecanoylsucrose, n-dodecyl-β-D-glucopyranoside, n-octyl-β-D-maltopyranoside, n-octyl-β-D-thioglucopyranoside, n-decanoylsucrose, n-decyl-β-D-maltopyranoside, n-decyl-β-D-thiomaltoside, n-heptyl-β-D-glucopyranoside, n-heptyl-β-D-thioglucopyranoside, n-hexyl-β-D-glucopyranoside, n-nonyl-β-D-glucopyranoside, n-octanoylsucrose, n-octyl-β-D-glucopyranoside, cyclohexyl-n-hexyl-β-D-maltoside, cyclohexyl-n-methyl-β-D-maltoside, digitonin, and those available under the trade designations PLURONIC, TRITON, TWEEN, as well as numerous others commercially available and listed in the Kirk Othmer Technical Encyclopedia. Examples are listed in Table 1 below. Preferred surfactants are the polyoxyethylene surfactants. More preferred surfactants include octyl phenoxy polyethoxyethanol.

TABLE 1

| SURFACTANT TRADE NAME | NONIONIC SURFACTANT | SUPPLIER |
|---|---|---|
| PLURONIC F127 | Modified oxyethylated alcohol and/or oxypropylated straight chain alcohols | Sigma St. Louis, MO |
| TWEEN 20 | Polyoxyethylene (20) sorbitan monolaurate | Sigma St. Louis, MO |
| TRITON X-100 | t-Octyl phenoxy polyethoxyethanol | Sigma St. Louis, MO |
| BRIJ 97 | Polyoxyethylene (10) oleyl ether | Sigma St. Louis, MO |
| IGEPAL CA-630 | Octyl phenoxy poly (ethyleneoxy) ethanol | Sigma St. Louis, MO |
| TOMADOL 1-7 | Ethoxylated alcohol | Tomah Products Milton, WI |
| Vitamin E TPGS | d-Alpha tocopheryl polyethylene glycol 1000 | Eastman Kingsport, TN |

Also suitable are fluorinated nonionic surfactants of the type disclosed in U.S. Pat. Nos. 6,664,354 (Savu et al.) and 6,852,781 (Savu et al.). Other nonionic fluorinated surfactants include those available under the trade designation ZONYL from DuPont (Wilmington, Del.).

Zwitterionic Surfactants. A wide variety of suitable zwitterionic surfactants are known that can be used as a coating on the solid phase material, as a lysing reagent, and/or as an eluting reagent. They include, for example, alkylamido betaines and amine oxides thereof, alkyl betaines and amine oxides thereof, sulfo betaines, hydroxy sulfo betaines, amphoglycinates, amphopropionates, balanced amphopolycarboxyglycinates, and alkyl polyaminoglycinates. Proteins have the ability of being charged or uncharged depending on the pH; thus, at the right pH, a protein, preferably with a pI of about 8 to 9, such as modified Bovine Serum Albumin or chymotrypsinogen, could function as a zwitterionic surfactant. A specific example of a zwitterionic surfactant is cholamido propyl dimethyl ammonium propanesulfonate available under the trade designation CHAPS from Sigma. More preferred surfactants include N-dodecyl-N,N dimethyl-3-ammonia-1-propane sulfonate.

Cationic Surfactants. A wide variety of suitable cationic surfactants are known that can be used as a lysing reagent, an eluting reagent, and/or as a coating on the solid phase material. They include, for example, quaternary ammonium salts, polyoxyethylene alkylamines, and alkylamine oxides. Typically, suitable quaternary ammonium salts include at least one higher molecular weight group and two or three lower molecular weight groups are linked to a common nitrogen atom to produce a cation, and wherein the electrically-balancing anion is selected from the group consisting of a halide (bromide, chloride, etc.), acetate, nitrite, and lower alkosulfate (methosulfate etc.). The higher molecular weight substituent(s) on the nitrogen is/are often (a) higher alkyl group (s), containing about 10 to about 20 carbon atoms, and the lower molecular weight substituents may be lower alkyl of about 1 to about 4 carbon atoms, such as methyl or ethyl, which may be substituted, as with hydroxy, in some instances. One or more of the substituents may include an aryl moiety or may be replaced by an aryl, such as benzyl or phenyl. Among the possible lower molecular weight substituents are also lower alkyls of about 1 to about 4 carbon atoms, such as methyl and ethyl, substituted by lower polyalkoxy moieties such as polyoxyethylene moieties, bearing a hydroxyl end group, and falling within the general formula:

$$R(CH_2CH_2O)_{(n-1)}CH_2CH_2OH$$

where R is a (C1-C4)divalent alkyl group bonded to the nitrogen, and n represents an integer of about 1 to about 15. Alternatively, one or two of such lower polyalkoxy moieties having terminal hydroxyls may be directly bonded to the quaternary nitrogen instead of being bonded to it through the previously mentioned lower alkyl. Examples of useful quaternary ammonium halide surfactants for use in the present invention include but are not limited to methyl-bis(2-hydroxyethyl)coco-ammonium chloride or oleyl-ammonium chloride, (ETHOQUAD C/12 and O/12, respectively) and methyl polyoxyethylene (15) octadecyl ammonium chloride (ETHOQUAD 18/25) from Akzo Chemical Inc.

Anionic Surfactants. A wide variety of suitable anionic surfactants are known that can be used as a lysing reagent, an eluting reagent, and/or as a coating on the solid phase material. Surfactants of the anionic type that are useful include sulfonates and sulfates, such as alkyl sulfates, alkylether sulfates, alkyl sulfonates, alkylether sulfonates, alkylbenzene sulfonates, alkylbenzene ether sulfates, alkylsulfoacetates, secondary alkane sulfonates, secondary alkylsulfates and the like. Many of these can include polyalkoxylate groups (e.g., ethylene oxide groups and/or propylene oxide groups, which can be in a random, sequential, or block arrangement) and/or cationic counterions such as Na, K, Li, ammonium, a protonated tertiary amine such as triethanolamine or a quaternary ammonium group. Examples include: alkyl ether sulfonates such as lauryl ether sulfates available under the trade designation POLYSTEP B12 and B22 from Stepan Company, Northfield, Ill., and sodium methyl taurate available under the trade designation NIKKOL CMT30 from Nikko Chemicals Co., Tokyo, Japan); secondary alkane sulfonates available under the trade designation HOSTAPUR SAS, which is a sodium (C14-C17)secondary alkane sulfonates (alpha-olefin sulfonates), from Clariant Corp., Charlotte, N.C.; methyl-2-sulfoalkyl esters such as sodium methyl-2-sulfo(C12-C16) ester and disodium 2-sulfo(C12-C16)fatty acid available from Stepan Company under the trade designation ALPHASTE PC-48; alkylsulfoacetates and alkylsulfosuccinates available as sodium laurylsulfoacetate (trade designation LANTHANOL LAL) and disodiumlaurethsulfosuccinate (trade designation STEPANMILD SL3), both from Stepan Co.; and alkylsulfates such as ammoniumlauryl sulfate commercially available under the trade designation STEPANOL AM from Stepan Co.

Another class of useful anionic surfactants include phosphates such as alkyl phosphates, alkylether phosphates, aralkylphosphates, and aralkylether phosphates. Many of these can include polyalkoxylate groups (e.g., ethylene oxide groups and/or propylene oxide groups, which can be in a random, sequential, or block arrangement). Examples include a mixture of mono-, di- and tri-(alkyltetraglycolether)-o-phosphoric acid esters generally referred to as trilaureth-4-phosphate commercially available under the trade designation HOSTAPHAT 340KL from Clariant Corp., and PPG-5 ceteth 10 phosphate available under the trade designation CRODAPHOS SG from Croda Inc., Parsipanny, N.J., as well as alkyl and alkylamidoalkyldialkylamine oxides. Examples of amine oxide surfactants include those commercially available under the trade designations AMMONYX LO, LMDO, and CO, which are lauryldimethylamine oxide, laurylamidopropyldimethylamine oxide, and cetyl amine oxide, all from Stepan Co.

Elution Techniques

For embodiments that use a solid phase material for retaining inhibitors, the more concentrated region of the sample that includes nucleic acid-containing material (e.g., nuclei) and/or released nucleic acid can be eluted using a variety of eluting reagents. Such eluting reagents can include water (preferably RNAse free water), a buffer, a surfactant, which can be cationic, anionic, nonionic, or zwitterionic, or a strong base.

Preferably the eluting reagent is basic (i.e., greater than 7). For certain embodiments, the pH of the eluting reagent is at least 8. For certain embodiments, the pH of the eluting reagent is up to 10. For certain embodiments, the pH of the eluting reagent is up to 13. If the eluted nucleic acid is used directly in an amplification process such as PCR, the eluting reagent should be formulated so that the concentration of the ingredients will not inhibit the enzymes (e.g., Taq Polymerase) or otherwise prevent the amplification reaction.

Examples of suitable surfactants include those listed above, particularly, those known as SDS, TRITON X-100, TWEEN, fluorinated surfactants, and PLURONICS. The surfactants are typically provided in aqueous-based solutions, although organic solvents (alcohols, etc.) can be used, if desired. The concentration of a surfactant in an eluting reagent is preferably at least 0.1 weight/volume percent (w/v-%), based on the total weight of the eluting reagent. The concentration of a surfactant in an eluting reagent is preferably no greater than 1 w/v-%, based on the total weight of the eluting reagent. A stabilizer, such as polyethylene glycol, can optionally be used with a surfactant.

Examples of suitable elution buffers include TRIS-HCl, N-[2-hydroxyethyl]piperazine-N'-[2-ethanesulfonic acid] (HEPES), 3-[N-morpholino]propanesulfonic acid (MOPS), piperazine-N,N'-bis[2-ethanesulfonic acid] (PIPES), 2-[N-morpholino]ethansulfonic acid (MES), TRIS-EDTA (TE) buffer, sodium citrate, ammonium acetate, carbonate salts, and bicarbonates etc.

The concentration of an elution buffer in an eluting reagent is preferably at least 10 millimolar (mM). The concentration of a surfactant in an eluting reagent is preferably no greater than 2 weight percent (wt-%).

Typically, elution of the nucleic acid-containing material and/or released nucleic acid is preferably accomplished using an alkaline solution. Although not intending to be bound by theory, it is believed that an alkaline solution allows for improved binding of inhibitors, as compared to elution with water. The alkaline solution also facilitates lysis of nucleic acid-containing material. Preferably, the alkaline solution has a pH of 8 to 13, and more preferably 13. Examples of sources of high pH include aqueous solutions of NaOH, KOH, LiOH, quaternary nitrogen base hydroxide, tertiary, secondary or primary amines, etc. If an alkaline solution is used for elution, it is typically neutralized in a subsequent step, for example, with TRIS buffer, to form a PCR-ready sample.

The use of an alkaline solution can selectively destroy RNA, to allow for the analysis of DNA. Otherwise, RNAse can be added to the formulation to inactivate RNA, followed by heat inactivation of the RNAse. Similarly, DNAse can be added to selectively destroy DNA and allow for the analysis of RNA; however, other lysis buffers (e.g., TE) that do not destroy RNA would be used in such methods. The addition of RNAse inhibitor such as RNAsin can also be used in a formulation for an RNA preparation that is subjected to real-time PCR.

Elution is typically carried out at room temperature, although higher temperatures may produce higher yields. For example, the temperature of the eluting reagent can be up to 95° C. if desired. Elution is typically carried out within 10 minutes, although 1-3 minute elution times are preferred.

Additional Embodiments

In other cases, it may be desirable to isolate various cell types selectively using known density gradient materials. These density gradient materials include sucrose and other commercially available under the trade designations FICOLL (Amersham Biosciences, Piscataway, N.J.), PERCOLL (Amersham Biosciences, Piscataway, N.J.), HISTOPAQUE (Sigma, St. Louis, Mo.), ISOPREP (Robbins Scientific Corporation, Sunnyvale, Calif.), HISTODENZ (Sigma, St. Louis, Mo.), and OPTIPREP (Sigma, St. Louis, Mo.). The specific cells of interest, for example, peripheral blood mononuclear cells (PBMC's) can be selectively removed by the use of a variable valve device. After extraction of the specific cells of interest, PCR can be directly carried out after lysis as long as the gradient material is PCR compatible. In cases where the gradient material is not PCR compatible, care must be taken to ensure adequate dilution of the sample (e.g., with water or buffer) followed by concentration of cells and repeating this process a few times to produce a PCR ready sample. Alternatively, simply diluting significantly may be sufficient to produce a PCR ready sample For example, in one embodiment of the present invention, a method includes: providing a device including a loading chamber and a variable valved process chamber; placing whole blood in the loading chamber; transferring the whole blood to a valved process chamber; contacting the whole blood with a density gradient material; centrifuging the whole blood and density gradient material in the valved process chamber to form layers, at least one of which contains cells of interest; removing at least a portion of the layer containing the cells of interest; and lysing the separated cells of interest to release nucleic acid. In one aspect of this method, prior to lysing the separated cells of interest, the method includes diluting the separated cells of interest with water or buffer, optionally further concentrating the diluted layer to increase the concentration of cells of interest, optionally separating the further concentrated region, and optionally repeating this process of dilution followed by concentration and separation. In another aspect of this method, prior to lysing the separated cells of interest, the method includes diluting the separated cells of interest with water, preferably sufficiently to form a 20×-1000× dilution.

The inhibitors can be removed using solid phase materials, as described herein (as well as described in U.S. Patent Application Publication No. US2005/0142571, filed on May 24, 2004, entitled METHODS FOR NUCLEIC ACID ISOLATION AND KITS USING SOLID PHASE MATERIAL, prior to or after capture of viral particles onto the beads (for example, as discussed below). Such solid phase materials can be used in various methods and with various samples described herein.

In addition to this, the level of inhibitors can be reduced using concentration/separation/optional dilution steps, for example, as disclosed in U.S. Patent Application Publication No. US2005/0142663, filed on May 24, 2004, entitled METHODS FOR NUCLEIC ACID ISOLATION AND KITS USING A MICROFLUIDIC DEVICE AND CONCENTRATION STEP.

In other embodiments, it may be necessary to capture viral DNA/RNA in the white blood cell. In these cases, the white blood cells can be isolated using a variable valve and beads can be used to capture the viral DNA/RNA.

For example, beads can be functionalized with the appropriate groups to isolate specific cells, viruses, bacteria, proteins, nucleic acids, etc. The beads can be segregated from the sample by centrifugation and subsequent separation. The beads could be designed to have the appropriate density and sizes (nanometers to microns) for segregation. For example, in the case of viral capture, beads that recognize the protein coat of a virus can be used to capture and concentrate the virus prior to or after removal of small amounts of residual inhibitors from a serum sample.

Nucleic acids can be extracted out of the segregated viral particles by lysis. Thus, the beads could provide a way of concentrating relevant material in a specific region within a device, also allowing for washing of irrelevant materials and elution of relevant material from the captured particle.

Examples of such beads include, but are not limited to, crosslinked polystyrene beads available under the trade designation CHELEX from Bio-Rad Laboratories, Inc. (Hercules, Calif.), crosslinked agarose beads with tris(2-aminoethyl)amine, iminodiacetic acid, nitrilotriacetic acid, polyamines and polyimines as well as the chelating ion exchange resins commercially available under the trade designation DUOLITE C-467 and DUOLITE GT73 from Rohm and Haas (Philadelphia, Pa.), AMBERLITE IRC-748, DIAION CR11, DUOLITE C647. These beads are also suitable for use as the solid phase material as discussed above.

Other examples of beads include those available under the trade designations GENE FIZZ (Eurobio, France), GENE RELEASER (Bioventures Inc., Murfreesboro, Tenn.), and BUGS N BEADS (GenPoint, Oslo, Norway), as well as Zymo's beads (Zymo Research, Orange, Calif.) and DYNAL beads (Dynal, Oslo, Norway).

Other materials are also available for pathogen capture. For example, polymer coatings can also be used to isolate specific cells, viruses, bacteria, proteins, nucleic acids, etc. in certain embodiments of the invention. These polymer coatings could directly be spray-jetted, for example, onto the cover film of a device.

Viral particles can be captured onto beads by covalently attaching antibodies onto bead surfaces. The antibodies can be raised against the viral coat proteins. For example, DYNAL beads can be used to covalently link antibodies. Alternatively, synthetic polymers, for example, anion-exchange polymers, can be used to concentrate viral particles. Commercially available resins such as viraffinity (Biotech Support Group, East Brunswick, N.J.) can be used to coat beads or applied as polymer coatings onto select locations in a device to concentrate viral particles. BUGS N BEADS (GenPoint, Oslo, Norway) can, for example, be used for extraction of bacteria. Here, these beads can be used to capture bacteria such as *Staphylococcus, Streptococcus, E coli, Salmonella*, and *Clamydia* elementary bodies.

Thus, in one embodiment of the present invention when the sample includes viral particles or other pathogens (e.g., bacteria), a device can include solid phase material in the form of viral capture beads or other pathogen capture material. In this method, the sample contacts the viral capture beads. More specifically, in one case, the viral capture beads can be used only for concentration of virus or bacteria, for example, followed by segregation of beads to another chamber, ending with lysis of virus or bacteria. In another case, the beads can be used for concentration of virus or bacteria, followed by lysis and capture of nucleic acids onto the same bead, dilution of beads, concentration of beads, segregation of beads, and repeating the process multiple times prior to elution of captured nucleic acid.

In a specific embodiment, a method includes: providing a device including a loading chamber, a variable valved process chamber, and a separation chamber including pathogen capture material; placing whole blood in the loading chamber; transferring the whole blood to a valved process chamber; centrifuging the whole blood in the valved process chamber to form a plasma layer including one or more pathogens, a red blood cell layer, and an interfacial layer (therebetween) including white blood cells; transferring at least a portion of the plasma layer including the one or more pathogens to the separation chamber having pathogen capture material therein; separating at least a portion of the one or more pathogens from the pathogen capture material; and lysing the one or more pathogens to release nucleic acid.

Alternatively, if beads (or other pathogen capture material) are not the method of choice for viral capture (or other pathogen capture), then one may choose to pellet out viral particles from serum or plasma using an ultracentrifuge. These concentrated viral particles can be transferred to the device for lysing with a surfactant with the addition of an RNAse inhibitor, for example, if viral RNA needs to be isolated followed by an amplification reaction (RT-PCR).

If the downstream application of the nucleic acid is subjecting it to an amplification process such as PCR, then all reagents used in the method are preferably compatible with such process (e.g., PCR compatible). Furthermore, the addition of PCR facilitators may be useful, especially for diagnostic purposes. Also, heating of the material to be amplified prior to amplification can be beneficial.

In embodiments in which the inhibitors are not completely removed, the use of buffers, enzymes, and PCR facilitators can be added that help in the amplification process in the presence of inhibitors. For example, enzymes other than Taq Polymerase, such as rTth, that are more resistant to inhibitors can be used, thereby providing a huge benefit for PCR amplification. The addition of Bovine Serum Albumin, betaine, proteinase inhibitors, bovine transferrin, etc. can be used as they are known to help even further in the amplification process. Alternatively, one can use a commercially available product such as Novagen's Blood Direct PCR Buffer kit (EMD Biosciences, Darmstadt, Germany) for direct amplification from whole blood without the need for extensive purification.

Objects and advantages of this invention may be further illustrated by the following examples, but the particular materials and amounts thereof recited in these examples, as well as other conditions and details, should not be construed to unduly limit this invention.

EXAMPLES

Example 1

Preparation of Solid Phase Material: Ammonia Form with TRITON-X 100

A 3M No. 2271 EMPORE Extraction Chelating Disk was placed in a glass filter holder. The extraction disk was converted into the ammonia form, following the procedure printed on the package insert. The disk placed in a vial and was submerged in a 1% TRITON-X 100 (Sigma-Aldrich, St. Louis, Mo.) solution (0.1 gram (g) of TRITON-X 100 in 10 mL of water), mixing for about 6-8 hours on a Thermolyne Vari-Mix Model M48725 Rocker (Barnstead/Thermolyne, Dubuque, Iowa). The disk was placed in glass filter holder, dried by applying a vacuum for about 20 minutes (min), and then dried overnight at room temperature (approximately 21° C.), taking care not to wash or rinse the disk.

Example 2A

Effect of Inhibitor/DNA on PCR: Varying Inhibitor Concentration with Fixed DNA Concentration A dilution series of inhibitors were made prior to spiking with clean human genomic DNA in order to study the effect of inhibitor on PCR. To 10 μL of 15 nanograms per microliter (ng/μL) human genomic DNA, 1 μL of different Mix I (neat or dilutions thereof) was added (Samples 2—no inhibitor added, 2D—neat, 2E—1:10, 2F—1:30, 2G—1:100, 2H—1:300) and vortexed. Two (2) μL aliquots of each sample were taken for 20 μL PCR. The results are shown in Table 2.

Mix I: one hundred (100) μL of whole blood was added to 1 μL of neat TRITON-X 100. The solution was incubated at room temperature (approximately 21° C.) for about 5 minutes, vortexing the solution intermittently (for approximately 5 seconds every 20 seconds). The solution was investigated to make sure that it was transparent before proceeding to the next step. The solution was spun in an Eppendorf Model 5415D centrifuge at 400 rcf for about 10 minutes. Approximately 80 μL from the top of the microcentrifuge tube and designated Mix I.

Example 2B

Effect of Inhibitor/DNA on PCR: Varying DNA Concentration with Fixed Inhibitor Concentration To 10 μL of human genomic DNA, 1 μL of 1:3 diluted Mix I (described above) was added. DNA concentrations that were examined were the following: Samples 2J—15 ng/μL, 2K—7.5 ng/μL, 2L—3.75 ng/μL, 2M—1.5 ng/μL. Two (2) μL aliquots of each sample were taken for 20 μL PCR. The results are shown in Table 2.

Example 2C

Effect of Inhibitor/DNA on PCR: DNA with No Added Inhibitor

The following samples were prepared with 1 μL of water added to each DNA sample instead of inhibitor: Samples 2N—15 ng/μL, 2P—7.5 ng/μL, 2Q—3.75 ng/μL, 2R—1.5 ng/μL. Two (2) μL aliquots of each sample were taken for 20 μL PCR. The results are shown in Table 2.

TABLE 2

| Sample No. | Ct (duplicate samples) |
|---|---|
| 2 | 19.10 |
| | 19.06 |
| 2D | 13.94 |
| | 29.50 |
| 2E | 27.39 |
| | 26.22 |
| 2F | 21.44 |
| | 20.66 |
| 2G | 19.90 |
| | 19.30 |
| 2H | 19.90 |
| | 20.08 |
| 2J | 28.45 |
| | 28.61 |
| 2K | 29.16 |
| | 30.22 |
| 2L | 30.47 |
| | 29.96 |
| 2M | 28.43 |
| | 26.16 |
| 2N | 20.05 |
| | 19.80 |
| 2P | 20.74 |
| | 20.54 |
| 2Q | 21.95 |
| | 21.88 |
| 2R | 22.67 |
| | 23.10 |

Example 3

Procedure for Isolation of Genomic DNA from Whole Blood with the Use of a Chelating Solid Phase Material Six hundred (600) μL of whole blood was spun at 2500 rpm for 10 min. The supernatant was separated and discarded, and the buffy coat was extracted from the interfacial layer. Five (5) μL of buffy coat was added to five (5)μL of 2% TRITON-X. The solution was mixed thoroughly, and placed onto a 3M No. 2271 EMPORE Extraction Chelating Disk prepared as described in Example 1 using 10% TRITON-X 100 instead of 1% TRITON-X 100 as a loading solution. After the solution had soaked into the disk, the sample was extracted with a twenty (20) μL aliquot of 0.1M NaOH. The solution was briefly spun in an Eppendorf Model 5415D centrifuge at 400 rcf. An aliquot of eleven (11) μL of sample was heated for 3 min at 95° C., and then added to three (3) μL of 1 M TRIS-HCl (pH 7.4).

Example 4

Procedure for Isolation of Genomic DNA from Whole Blood

Six hundred (600) μL of whole blood was spun at 2500 rpm for 10 min. The supernatant was separated and discarded, and the buffy coat was extracted from the interfacial layer. Five (5) μL of buffy coat was added to the ninety five(95) μL of RNase-free sterile water. The solution was mixed until the color became uniform and spun in an Eppendorf Model 5415D centrifuge at 400 rcf for about 2 minutes. An aliquot of ninety five (95) μL of the solution from the top was separated and discarded, leaving about five (5) μL of concentrated material at the bottom of the centrifuge tube. To the last 5 μL of concentrated material, 95 μL of RNase-free sterile water was added. The sample was mixed until the color became uniform. The solution was spun in an Eppendorf Model 5415D centrifuge at 400 rcf for about 2 minutes. A 95 μL of the solution on the top was separated and discarded, leaving about ten (10) μL of concentrated material at the bottom of the centrifuge tube. To the last 10 μL of concentrated material, one (1) μL of 1 M NaOH was added. After 1 min incubation, the sample was heated for 3 min at 95° C. A 3 μL of 1 M TRIS-HCl (pH 7.4) was added to 11 μL of sample.

Results

Table 3 reports results that were obtained on ABI 7700 QPCR Machine (Applera, Foster City, Calif.) following the instructions in QuantiTech SYBR Green PCR Handbook on p. 10-12 for preparation of a 10 μL PCR sample (2 μL of sample in 10 μL SYBR Green Master Mix, 4 μL β-actin, 4 μL of water) for Examples 1-2; Results for Examples 3-4 were obtained on LightCycler 2.0 (Roche Applied Science, Indianapolis, Ind.) following the instructions in LightCycler Factor V Leiden Mutation Kit's package insert on p. 2-3 for preparation of a 10 μL PCR sample (2.5 μL of sample in 5.5 μL of RNase-free sterile water, 1 μL of 10× Factor V Leiden Reaction Mix and 1 μL of 10× Factor V Leiden Mutation Detection Mix). Spectra measurements were run on a SpectraMax Plus[384] spectrophotometer at 405 nm (Molecular Devices Corporation, Sunnyvale, Calif.). Two, three or four values for each sample represent duplicates, triplicates, or quadruplicates.

TABLE 3

| Samples | Ct | 405 nm (avg) |
|---|---|---|
| 1.5 ng/μL human genomic DNA in 0.1 M NaOH/40 mM TRIS-HCl buffer | 16.92<br>20.67 | — |
| 1.5 ng/μL human genomic DNA in water | 19.01<br>18.67 | 0 |
| 1.5 ng/μL human genomic DNA in water | 16.18<br>16.28 | — |
| Examples 2A and 2B Mix I diluted 1:36 | — | 2.63 |
| Examples 2A and 2B Mix I diluted 1:360 | — | 0.38 |
| Examples 2A and 2B Mix I diluted 1:3600 | — | 0.036 |
| Examples 2A and 2B Mix I diluted 1:36000 | — | 0 |
| Example 3* | 26.02, 24.93 | — |
| Example 4* | 22.73, 23.93 | — |

*Positive Control for Examples 3-4 was DNA extracted from two hundred (200) μL of whole blood following "Blood and Body Fluid Spin Protocol" described in QIAamp DNA Blood Mini Kit Handbook p. 27, eluting in 200 μL of water and had Ct value of 20-21.
Negative Control (NTC or no template control) did not amplify in these experiments.

As used herein and in the appended claims, the singular forms "a," "and," and "the" include plural referents unless the context clearly dictates otherwise. Thus, for example, reference to "a valve lip" includes a plurality of valve lips and reference to "the process chamber" includes reference to one or more process chambers and equivalents thereof known to those skilled in the art.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A valved process chamber on a sample processing device, the sample processing device configured to be rotated about an axis of rotation, the valved process chamber comprising:

a process chamber comprising a process chamber volume located between opposing first and second major sides of the sample processing device, wherein the process chamber occupies a process chamber area on the sample processing device, and wherein the process chamber includes an axis that is oriented substantially radially with respect to the axis of rotation; and a valve chamber located at least partially within the process chamber area, the valve chamber located between the process chamber volume and the second major side of the sample processing device, wherein the valve chamber is isolated from the process chamber by a valve septum separating the valve chamber and the process chamber, wherein a portion of the process chamber volume lies between the valve septum and the first major side of the sample processing device, and wherein the valve septum has a length that extends along or substantially parallel to the axis of the process chamber, such that the valve septum is configured to allow for adjustment of the location, along the length of the valve septum, at which fluid communication is provided between the process chamber and the valve chamber, such that the location is positioned to allow a selected portion of material in the process chamber located closer to the axis of rotation than the location to exit the process chamber when the sample processing device is rotated about the axis of rotation.

2. A valved process chamber according to claim 1, further comprising a detection window located at least partially within the process chamber area, wherein the detection window is transmissive to selected electromagnetic energy directed into and/or out of the process chamber volume.

3. A valved process chamber according to claim 2, wherein the detection window is coextensive along the length of the process chamber with the valve septum.

4. A valved process chamber according to claim 2, wherein the detection window is formed through the first major side of the sample processing device.

5. A valved process chamber according to claim 2, wherein the detection window is formed through the second major side of the sample processing device.

6. A valved process chamber according to claim 2, wherein the valve chamber and the detection window occupy mutually exclusive portions of the process chamber area.

7. A valved process chamber according to claim 1, wherein the length is a first length, wherein the process chamber has a second length that extends along or substantially parallel to the axis, and wherein the first length is less than the second length.

8. A valved process chamber according to claim 1, wherein the length is a first length, wherein the process chamber has a second length that extends along or substantially parallel to the axis, and wherein the first length includes at least a portion that extends along at least 30% of the second length.

9. A valved process chamber according to claim 1, wherein the valve septum extends along a length of the process chamber area for 30% or more of a maximum length of the process chamber area.

10. A valved process chamber according to claim 1, wherein the valve septum extends for a length of 1 millimeter or more along the length of the process chamber.

11. A valved process chamber according to claim 1, wherein the sample processing device is opaque between the process chamber volume and the first major side of the sample processing device.

12. A valved process chamber according to claim 1, wherein at least a portion of the valve chamber is located within a valve lip extending into the process chamber area, and wherein the valve septum is formed in the valve lip.

13. A valved process chamber according to claim 12, wherein the valve lip occupies only a portion of the width of the process chamber area.

14. A valved process chamber according to claim 13, further comprising a detection window located within the process chamber area, wherein the detection window is transmissive to selected electromagnetic energy directed into and/or out of the process chamber volume, and wherein the detection window occupies at least a portion of the width of the process chamber area that is not occupied by the valve lip.

15. A valved process chamber on a sample processing device, the sample processing device configured to be rotated about an axis of rotation, the valved process chamber comprising:

a process chamber comprising a process chamber volume located between opposing first and second major sides of the sample processing device, wherein the process chamber occupies a process chamber area on the sample processing device, and wherein the process chamber includes an axis that is oriented substantially radially with respect to the axis of rotation; and a valve chamber located at least partially within the process chamber area, the valve chamber located between the process chamber volume and the second major side of the sample processing device, wherein the valve chamber is isolated from the process chamber by a valve septum separating the valve chamber and the process chamber, wherein a portion of the process chamber volume lies between the valve septum and the first major side of the sample processing device, and wherein the valve septum has a length that extends along or substantially parallel to the axis of the process chamber; and an opening in the valve septum at a selected location along the length of the valve septum to provide fluid communication between the process chamber and the valve chamber, the opening positioned to allow a selected portion of material in the process chamber located closer to the axis of rotation than the opening to exit the process chamber when the sample processing device is rotated about the axis of rotation.

16. A valved process chamber according to claim 15, further comprising a detection window located at least partially within the process chamber area, wherein the detection window is transmissive to selected electromagnetic energy directed into and/or out of the process chamber volume.

17. A valved process chamber according to claim 16, wherein the detection window is coextensive along the length of the process chamber with the valve septum.

18. A valved process chamber on a sample processing device, the sample processing device configured to be rotated about an axis of rotation, the valved process chamber comprising:

a process chamber comprising a process chamber volume located between opposing first and second major sides of the sample processing device, wherein the process chamber occupies a process chamber area on the sample processing device that is generally defined by a length and a width transverse to the length, and wherein the length of the process chamber is oriented substantially radially with respect to the axis of rotation; and a valve chamber located at least partially within the process chamber area, the valve chamber located between the process chamber volume and the second major side of the sample processing device, wherein the valve chamber is isolated from the process chamber by a valve septum separating the valve chamber and the process chamber, wherein a portion of the process chamber volume lies between the valve septum and the first major side of the sample processing device, wherein the valve septum has a length that extends along or substantially parallel to the length of the process chamber, wherein the valve septum includes a width transverse to the length, and wherein at least a portion of the width of the valve chamber is located within a valve lip extending into and overhanging the process chamber, and wherein the valve septum is formed in the valve lip.

19. A valved process chamber according to claim 18, further comprising a detection window located at least partially within the process chamber area, wherein the detection window is transmissive to selected electromagnetic energy directed into and/or out of the process chamber volume.

20. A valved process chamber according to claim 19, wherein the detection window is coextensive along the length of the process chamber with the valve septum.

* * * * *

UNITED STATES PATENT AND TRADEMARK OFFICE

CERTIFICATE OF CORRECTION

PATENT NO. : 8,057,758 B2
APPLICATION NO. : 12/719704
DATED : November 15, 2011
INVENTOR(S) : William Bedingham It is certified that error appears in the above-identified patent and that said Letters Patent is hereby corrected as shown below:

Title Page 4, item (56): Column 1, Other Publications
Line 7, Delete "QIAmp" and insert -- QIAAmp --, therefor.
Line 13, Delete "faeclis" and insert -- faecalis --, therefor.
Line 24, Delete "Quantitaion" and insert -- Quantitation --, therefor.
Line 26, Delete "Finaly" and insert -- Final --, therefor.
Line 36, Delete "detrilyated" and insert -- detritylated --, therefor.
Line 39, Delete "Segragation" and insert -- Segregation --, therefor.
Line 52, Delete "Quantitive" and insert -- Quantitative --, therefor.

Title Page 4, item (56): Column 2, Other Publications
Line 6-7, Delete "Minaturized" and insert -- Miniaturized --, therefor.
Line 7, Delete "Analyitical" and insert -- Analytical --, therefor.
Line 23, Delete "RapTract" and insert -- Rap Extract --, therefor.

Column 5
Line 8, Delete "archeobacteriae" and insert -- archaebacteria --, therefor.

Column 18
Line 38, Delete "is to" and insert -- is --, therefor.
Line 47, Delete "Stonger" and insert -- Stronger --, therefor.
Line 57, Delete "bacterial" and insert -- bacteria --, therefor.

Column 24
Line 16, Delete "chondritin" and insert -- chondroitin --, therefor.

Column 27
Line 6, Delete "Parsipanny," and insert -- Parsippany, -- therefor.

Signed and Sealed this
Twenty-fourth Day of January, 2012

David J. Kappos

David J. Kappos
*Director of the United States Patent and Trademark Office*

Column 28
Line 40, Delete “sample” and insert -- sample. --, therefor.

Column 29
Line 67, Delete “Clamydia” and insert -- Chlamydia --, therefor.